US007236891B2

(12) United States Patent
Davies et al.

(10) Patent No.: US 7,236,891 B2
(45) Date of Patent: Jun. 26, 2007

(54) METHODS OF DETERMINING POLYPEPTIDE STRUCTURE AND FUNCTION

(75) Inventors: Peter L. Davies, Kingston (CA); John S. Elce, Kingston (CA); Christopher Hosfield, Toronto (CA); Zongchao Jia, Kingston (CA); Tudor Moldoveanu, Kingston (CA)

(73) Assignee: Queen's University at Kingston, Kingston, Ontario (CA)

( * ) Notice: Subject to any disclaimer, the term of this patent is extended or adjusted under 35 U.S.C. 154(b) by 328 days.

(21) Appl. No.: 10/157,016

(22) Filed: May 30, 2002

(65) Prior Publication Data

US 2003/0017984 A1    Jan. 23, 2003

Related U.S. Application Data

(60) Provisional application No. 60/293,984, filed on May 30, 2001.

(51) Int. Cl.
*G06F 17/00* (2006.01)
*G06F 17/30* (2006.01)

(52) U.S. Cl. .......................... 702/27; 702/19; 530/350

(58) Field of Classification Search ............... 702/27, 702/19
See application file for complete search history.

(56) References Cited

OTHER PUBLICATIONS

Li R, et al. Structure-based design of parasitic protease inhibitors. Bioorg Med Chem. Sep. 1996;4(9):1421-7.*
Hosfield CM, Elce JS, Davis PL, Jia Z. Crystal structure of calpain reveals the structural basis for Ca(2+)-dependent protease activity and a novel mode of enzyme activation. EMBO J. Dec. 15, 1999;18(24):6880-9.☐☐*
Protein Databank SearchFields, URL=http://www.rcsb.org/pdb/cgi/queryForm.cgi.*
Kellog, URL=http://www.phc.vcu.edu/Kellogg_postdoc_position.html.*
Seeman, N, Current Crystallization Protocol, URL=http://seemanlab4.chem.nyu.edu/nano-pro.html.*
Sorimachi, H., et al., "The Structure of Calpain." *J. Biochem.* 129:653-664 (2001).

* cited by examiner

*Primary Examiner*—Michael Borin
(74) *Attorney, Agent, or Firm*—Stephen J. Scribner; Carol Miernicki Steeg

(57) ABSTRACT

The present invention provides methods for determining the structure and/or function of one or more domains of a cation-dependent (and preferably calcium-dependent) polypeptide (particularly a calcium-dependent enzyme, which may be a protease such as calpain) in the presence of one or more cations. The invention further provides methods for identifying a ligand having the ability to bind to one or more ligand-binding domains (LBDs) of a cation-dependent (and preferably calcium-dependent) polypeptide, and ligands identified by these methods. The invention also provides methods of treating or preventing physical disorders in animals using these ligands.

23 Claims, 11 Drawing Sheets

METHODS OF DETERMINING POLYPEPTIDE STRUCTURE AND FUNCTION

RELATED APPLICATION

This application claims the benefit of the filing date of U.S. Provisional Patent Application Ser. No. 60/293,984, filed on May 30, 2001, the disclosure of which is hereby incorporated by reference in its entirety.

BACKGROUND OF THE INVENTION

1. Field of the Invention

The present invention generally pertains to the fields of molecular biology, protein crystallization, x-ray diffraction analysis, three-dimensional structural determination, rational drug design and molecular modeling of related proteins. The invention provides methods for determining the structure or function of one or more domains of a cation-dependent (and preferably calcium-dependent) polypeptide in the presence of one or more cations. The invention further provides methods for identifying a ligand having the ability to bind to one or more ligand-binding domains (LBDs) of a cation-dependent (and preferably calcium-dependent) polypeptide, and ligands identified by these methods. Finally, the invention provides methods of treating or preventing physical disorders in animals using these ligands.

2. Background Art

Protein Domain Analysis. Large proteins are typically made up of more than one domain and sometimes more than one subunit. This can complicate structure determination by X-ray crystallography if an attribute of any one part of the molecule is inhibitory to crystallization. Sometimes the overall flexibility of the multidomain structure can make it difficult for the protein to crystallize. In addition, large proteins (>40 kDa) are out of the range for structure determination by NMR techniques. One approach to circumvent these problems is to try to split the protein into domains and determine the structure in a piece-by-piece fashion. Here it is helpful to have information from sequence comparisons and or partial proteolysis to delineate the domain boundaries.

Calpains. The conventional calpains, better known as the m- and μ-calpains, are mammalian cellular cysteine proteases activated by $Ca^{2+}$. They are the founding members of the calpain superfamily, which contains isoforms from mammals to various organisms such as *Drosophila melanogaster* and *Caenorhabditis elegans* (Sorimachi, H. and Suzuki, K. *J. Biochem.* (Tokyo) 129:653–664 (2001)). They function in $Ca^{2+}$ signaling by modulating biological activities of their substrates through limited proteolysis (Sorimachi, H. and Suzuki, K. *J. Biochem.* (Tokyo) 129:653–664 (2001)). The conventional calpains are indispensable during development as indicated by knockout mice lethality (Arthur, J. S., et al., *Mol. Cell Biol.* 20:4474–4481 (2000); Zimmerman, U. J., et al., *IUBMB. Life* 50:63–68 (2001)) and they have been implicated in apoptosis (Wang, K. K., *Trends Neurosci.* 23:59 (2000)), cell cycle (Santella, L., et al. *Cell Calcium* 23:123–130 (1998)), and cell motility (Cox, E. A. and Huttenlocher, A., *Microsc. Res. Tech.* 43:412–419 (1998)). While physiological $Ca^{2+}$ levels inside the cell are too low (<1 μM) for uncontrolled activation of either m- (>100 μM) or μ-calpain (>5 μM) (Croall, D. E., and DeMartino, G. N., *Physiol Rev.* 71:813–847 (1991)), during certain pathological states cellular $Ca^{2+}$ levels can increase enough to achieve calpain activation without the aid of putative endogenous activators. Under such circumstances unrestrained proteolysis by calpains can result in tissue damage seen during ischemic injury (heart, brain)(Wang, K. K., and Yuen, P. W., *Trends Pharmacol. Sci.* 15: 412–419 (1994); Lee, K. S., et al., *Ann. N. Y. Acad. Sci.* 825: 95–103 (1997)) and neurodegeneration (Alzheimer's disease) (Patrick, G. N., et al. *Nature* 402: 615–622 (1999); Lee, M.S., et al. *Nature* 405: 360–364 (2000); Nixon, R. A., *Ann. N. Y. Acad. Sci.* 924: 117–131 (2000)). Administering existing calpain inhibitors has proven to lessen or prevent the onset of such conditions, but the lack of specific calpain inhibitors weakens the effectiveness of such therapies (Wang, K. K., and Yuen, P. W., *Trends Pharmacol. Sci.* 15: 412–419 (1994)).

The crystal structures of rat (Hosfield, C. M., et al., *EMBO J* 18:6880–6889 (1999)) and human (Strobl, S., et al., *Proc. Natl. Acad. Sci. U.S.A.* 97:588–592 (2000)) m-calpain heterodimers determined in the absence of $Ca^{2+}$ have revealed a circular arrangement of domains. The circle extends from the anchor peptide (~20 residues) at the N terminus of the large subunit (80 kDa), through the cysteine protease region (domains I~190 residues and II~145 residues), along the C2-like domain III (~160 residues), down the linker (~15 residues) and into the EF-hand-containing domain IV (~170 residues). Domain W makes intimate contacts with the homologous 28 kDa small subunit (domain VI) through pairing of their fifth EF-hands, and the small subunit completes the ring by binding to the anchor peptide. Domain V of the small subunit is invisible in the human heterodimer structure likely due to its high content of glycine residues. In this circular structure, domains I and II are held slightly apart and miss-aligned such that the active site cleft is too wide for catalysis. Activation by $Ca^{2+}$ must realign domains I and II to bring the catalytic residues in register for peptide bond hydrolysis. However, in the absence of a $Ca^{2+}$-bound crystal structure the mechanism of activation of calpain remains controversial (Sorimachi, H. and Suzuki, K. *J. Biochem.* (Tokyo) 129: 653–664 (2001)). Although it is not clear if, and how, $Ca^{2+}$ binding to the EF-hand domains initiates activation, some of the early events in this process, such as the autoproteolytic removal of the anchor peptide and/or the release of the small subunit, break the protein circle and lead to a general increase in susceptibility to proteolysis (Moldoveanu, T., et al., *Biochim. Biophys. Acta* 1545: 245–254 (2001)). It has heretofore been unknown whether these conformational changes release the constraints on domains I and II and allow them to form an active protease.

The difficulty in solving the structure of the calpain heterodimer in the presence of $Ca^{2+}$ arises from subunit dissociation, often followed by large subunit aggregation under crystallization conditions. Nevertheless, a desirable template for rational drug design would be the assembled active site. The present invention provides such assembled active sites, and methods for producing and using such active sites.

BRIEF SUMMARY OF THE INVENTION

The present invention provides methods for determining the structure or function of one or more domains of cation-dependent (and preferably calcium-dependent) polypeptides, particularly enzymes, in the presence of one or more cations. The methods involve providing a recombinant host cell expressing one or more domains of the polypeptides, or producing peptides synthetically; isolating these polypeptide domains expressed by the recombinant host cell; crystallizing the isolated polypeptide domains in the presence of one or more cations; and determining the structural and/or functional features of the crystallized polypeptide domains. In one embodiment of the method, the cation-dependent polypeptide is dependent upon a divalent cation for structure and/or function, such as $Ca^{2+}$, $Mg^{2+}$, $Mn^{2+}$ and $Zn^{2+}$, most preferably $Ca^{2+}$.

In a preferred embodiment of the method, the polypeptide domain may be ligand-binding domains of a cation-dependent (and preferably calcium-dependent) polypeptide, such as an enzyme active site. In one such embodiment, the cation-dependent (and preferably calcium-dependent) polypeptide is an enzyme. In certain preferred such embodiments, the enzyme is a protease, a nucleic acid polymerase, a transferase, a phosphatase or a kinase. In a particularly preferred such embodiment, the enzyme may be a $Ca^{2+}$-dependent protease such as calpain or an isoform thereof, particularly, m-calpain or μ-calpain, or a mutant, variant or derivative thereof.

The present invention also provides an isolated polypeptide comprising one or more domains of a calcium-dependent enzyme produced by the methods of the invention. The methods involve providing a recombinant host cell expressing said one or more domains of said enzyme; isolating said one or more enzyme domains expressed by said recombinant host cell; and crystallizing said one or more isolated enzyme domains in the presence of one or more cations. In one aspect of the invention, the calcium-dependent enzyme is a calcium-dependent protease, such as calpain or an isoform thereof. In one embodiment, the calcium-dependent protease is m-calpain, μ-calpain, or a mutant, variant or derivative thereof. In another embodiment, the isolated enzyme domains bind one or more ligands, and these domains comprise one or more active sites of the enzyme. In a preferred embodiment, the domains comprise domain I of calpain or an isoform thereof, domain II of calpain or an isoform thereof or both domains I and II of calpain or an isoform thereof.

A variety of methods can be used to determine the active site domains of cation-dependent (and preferably calcium-dependent) enzymes. These methods include, but are not limited to, evolutionary conservation analysis, truncation analysis and mutation analysis.

According to the method of the invention, the host cell for the expression of the domain polypeptide can be prokaryotic or eukaryotic. Preferred hosts include E. coli, Bacillus species, yeast, and insect and mammalian cells.

The invention further provides methods for crystallizing one or more domains of cation-dependent (and preferably calcium-dependent) polypeptides in the presence of one or more cations. Such methods of the invention may involve, for example, providing a purified polypeptide comprising said domain; and crystallizing said purified polypeptide using a method selected from hanging drop, microbatch, sitting-drop or dialysis. By the invention, the crystallized domain is resolvable using X-ray crystallography to obtain X-ray diffraction patterns having a maximum resolution in the range of about 1.5–3.5 Å. In one such aspect of the invention, the polypeptide comprising the domain can be crystallized in the presence of a ligand.

In one embodiment of the method, the binding of a ligand to the ligand binding domain of the cation-dependent (and preferably calcium-dependent) polypeptide modulates the function of the polypeptide, and may induce structural (e.g. conformational) changes in the polypeptide. In a preferred embodiment, the ligand inhibits or reduces the activity of the polypeptide. In another preferred emobediment, the ligand activates or increases the activity of the polypeptide. In another embodiment, the ligand is a substrate for the polypeptide.

The invention further provides methods for designing ligands capable of binding to domains of a cation-dependent (and preferably calcium-dependent) polypeptide. One such method involves providing a model of the crystal structure of the ligand-binding domain (LBD) of the polypeptide; analyzing the model to design a ligand which binds to the LBD; and determining the effect of the ligand on the structure and/or activity of the polypeptide.

The invention further provides methods of quantifying in a solution the amount of ligand bound to a polypeptide LBD. One such method involves adding a ligand to a polypeptide LBD, exciting the domain by illumination with light of wavelength of about 260 to 300 nm, and measuring fluorescence emission at about 320 to 360 nm, wherein a reduction in emission by the polypeptide domain relative to a control polypeptide domain illuminated in the absence of the ligand indicates binding of the ligand to the polypeptide domain. In a preferred embodiment, the polypeptide domain is excited at about 280 nm, and the fluorescence emission is measured at about 340 nm.

The invention further provides a computer-based system which includes a data-storage means for storing data corresponding to the crystal structure of the ligand binding domain, and a data-analyzing means such as a computer program for analyzing data stored in the data-storage means for designing ligands capable of binding to the ligand binding domain of said cation-dependent (and preferably calcium-dependent) polypeptide.

The invention further provides methods for identifying ligands having the ability to bind to one or more ligand-binding domains of a cation-dependent (and preferably calcium-dependent)polypeptide. One such method involves providing a recombinant host cell expressing said one or more polypeptide ligand-binding domains; isolating said one or more polypeptide domains expressed by said recombinant host cell; mixing said one or more isolated polypeptide domains with one or more ligands; co-crystallizing said one or more isolated polypeptide domains with said ligands in the presence of said one or more cations; determining the structural and or functional features of said crystallized polypeptide domains; and determining the ability of said one or more ligands to bind to said one or more ligand-binding domains.

In a preferred embodiment of the method, ligands are identified for the LBD of a cation-dependent (and preferably calcium-dependent) polypeptide, which is an enzyme active site. In additional preferred embodiments, the enzyme is a protease, a nucleic acid polymerase, a transferase, a phosphatase or a kinase. In a particularly preferred such embodiment, the enzyme may be a $Ca^{2+}$-dependent protease such as calpain or an isoform thereof, particularly, m-calpain or μ-calpain, or a mutant, variant or derivative thereof.

The invention further provides ligands identified by the method described above. In a preferred embodiment, the ligand induces a conformational change in the cation-dependent (and preferably calcium-dependent) polypeptide. In another preferred embodiment, the ligand modulates the function of the cation-dependent (and preferably calcium-dependent) polypeptide. In one embodiment, the ligand activates or increases the activity of the polypeptide. In another embodiment, the ligand inhibits or decreases the activity of the polypeptide. The ligand can also be the substrate for the cation-dependent (and preferably calcium-dependent) polypeptide. In a preferred embodiment the ligand binds to ligand-binding domains of a cation-dependent (and preferably calcium-dependent) polypeptide, which is an enzyme active site. In additional preferred embodiments, the enzyme is a protease, a nucleic acid polymerase, a transferase, a phosphatase or a kinase. In a particularly preferred such embodiment, the enzyme may be a $Ca^{2+}$-dependent protease such as calpain or an isoform thereof, particularly, m-calpain or µ-calpain, or a mutant, variant or derivative thereof.

The invention further provides methods of treating or preventing a disease or physical disorder in an animal comprising administering to an animal suffering from or predisposed to the disease or physical disorder an effective amount of one or more ligands identified by the method of the present invention. The disorders that can be treated or prevented by such methods of the invention include, but are not limited to, cardiovascular disorder (such as stroke, myocardial infarction, heart disease and the like), Alzheimer's disease and other disorders that involve cation-dependent (and preferably calcium-dependent) polypeptides or enzymes. In a preferred embodiment, the animal is a mammal, most preferably a human. According to the methods of the present invention the ligand can be administered in pure form, or in a composition further comprising a pharmaceutically acceptable excipient. The invention also provides a composition comprising the ligand and a pharmaceutically acceptable excipient.

One embodiment of the present invention is the resolution of the structural and functional domains of calpain, a $Ca^{2+}$-dependent cysteine protease. The inventors have gathered structural and biochemical evidence which suggests that domains I+II (about 40 kDa, variability introduced by the measurement method), a segment that is evolutionarily conserved among distant cellular organisms, has the minimal functional and structural requirement of a $Ca^{2+}$-dependent cysteine protease. In this context, the activity observed only in the presence of $Ca^{2+}$ correlates with a conformational change that is significantly different in the absence of $Ca^{2+}$. The 2.1 Å crystal structure of the active site construct in the presence of $Ca^{2+}$ defines this conformation and provides insights into the unique mechanism of activation by $Ca^{2+}$. Two novel $Ca^{2+}$ binding sites, one in each domain, are conserved among various calpain isoforms. The $Ca^{2+}$ binding at these sites is highly cooperative and this can be inferred from the structure. The structural rearrangement induced by $Ca^{2+}$ in domains I and II ultimately results in alignment of active site residues for catalysis similar to other known cysteine proteases. Aside from extending the basis of $Ca^{2+}$ regulation of the conventional calpains, these data shed light on the mechanism of activation of any of the calpain isoforms that lack domains III and IV of the large subunit and/or the small subunit but retain the structural determinants of a $Ca^{2+}$ dependent protease through the active site region.

In another aspect, the invention provides a method of designing a ligand for binding with an active site of a calpain in the presence of $Ca^{2+}$, wherein said active site comprises at least a portion of domains I and II of said calpain, the method comprising: computationally evolving a ligand using a computer-based system for rational design of ligands so that said evolved ligand binds with said active site comprising at least a portion of domains I and II of calpain; and outputting a representation of said computationally-evolved ligand.

In various embodiments, said calpain may be m-calpain, µ-calpain, or a mutant, variant, isoform, or derivative thereof. The ligand may modulate activity or structure of said calpain upon binding to said active site. The ligand may inhibit or reduce the activity of said calpain. In another embodiment, the ligand may activate or enhance the activity of said calpain. In a further embodiment, binding of said ligand to said active site induces a conformational change in said calpain. In another embodiment, said ligand is a substrate for said calpain. In a preferred embodiment, the active site comprises residue C115 or S115 of said calpain.

According to another aspect of the invention, there is provided a method of identifying a ligand to bind with an active site of a calpain in the presence of $Ca^{2+}$, wherein said active site comprises at least a portion of domains I and II of said calpain, the method comprising: providing a model of the three dimensional structure of said active site in the presence of $Ca^{2+}$; providing a database containing molecules coded for spatial occupancy, relative atomic position, bond type and/or charge; screening said data base to select a ligand that can bind with said active site; and outputting a representation of said selected ligand.

In various embodiments, said calpain may be m-calpain, µ-calpain, or a mutant, variant, isoform, or derivative thereof. The ligand may modulate activity or structure of said calpain upon binding to said active site. The ligand may inhibit or reduce the activity of said calpain. In another embodiment, the ligand may activate or enhance the activity of said calpain. In a further embodiment, binding of said ligand to said active site induces a conformational change in said calpain. In another embodiment, said ligand is a substrate for said calpain. In a preferred embodiment, said active site comprises residue C115 or S115 of said calpain.

In another aspect, the invention provides a method of identifying a ligand to bind with an active site of a calpain in the presence of $Ca^{2+}$, wherein said active site comprises at least a portion of domains I and II of said calpain, the method comprising: providing an isolated polypeptide comprising said active site; mixing a ligand with said isolated polypeptide to form a mixture; and analyzing said mixture for binding of said ligand to said active site.

In a preferred embodiment, said isolated polypeptide comprises calpain residue S115. In one embodiment, analyzing said mixture comprises: illuminating said mixture with light at a wavelength of about 260 to 300 nm; and measuring an amount of fluorescence emitted by said mixture at a wavelength of about 320 to 360 nm, wherein a reduction in emission by said mixture relative to a control illuminated in the absence of said ligand indicates binding of said ligand to said active site. In various embodiments, said mixture is illuminated with light at a wavelength of about 280 nm, and/or the fluorescence emission is measured at a wavelength of about 340 nm.

In another aspect, the invention provides a method of identifying a ligand to bind with an active site of a calpain in the presence of $Ca^{2+}$, wherein said active site comprises at least a portion of domains I and II of said calpain, the method comprising: providing said calpain domains I and II in the presence of $Ca^{2+}$; mixing said domains I and II with one or more ligands; crystallizing said domains I and II with said one or more ligands in the presence of $Ca^{2+}$; and determining the ability of said one or more ligands to bind to said active site.

In a preferred embodiment, said domains I and II comprise calpain residue S115. In various embodiments, said one or more ligands modulate(s) the function or structure of said calpain upon binding to said active site. Binding of said one or more ligands to said active site may inhibit or reduce activity of said calpain. In another embodiment, binding of said one or more ligands to said active site may activate or enhance activity of said calpain. In yet another embodiment, binding of said one or more ligands to said active site induces a conformational change in said calpain. In a further embodiment, said ligand is a substrate for said calpain.

In another aspect, the invention provides an isolated polypeptide comprising an active site of calpain in the presence of $Ca^{2+}$, wherein said active site comprises at least a portion of domains I and II of said calpain.

In one embodiment, the isolated polypeptide may be produced by a method comprising: providing a recombinant host cell expressing said domains I and II; isolating said domains I and II expressed by said recombinant host cell; and crystallizing said isolated domains in the presence of $Ca^{2+}$. In various embodiments said calpain may be m-calpain, μ-calpain, or an isoform, mutant, variant or derivative thereof. In a preferred embodiment, said polypeptide comprises calpain residue S115.

Other preferred embodiments of the present invention will be apparent to one of ordinary skill in light of the following drawings and description of the invention, and of the claims.

(A). Proteolysis of inactive C105S recombinant m-calpain heterodimer (80K/21K) by μI-II (about 40 KDa) was performed in the presence of 1 mM $CaCl_2$ at an enzyme to substrate ratio of 1:66 as described in Experimental Procedures. At the times indicated (in minutes; h, hours) aliquots of the reaction were quenched with SDS sample buffer. A representative SDS-PAGE profile is shown. Molecular weight standard ladder (M) is shown at the right.

(B) Intrinsic tryptophan fluorescence intensity was monitored at 340 nm by exciting μI-II sample at 280 nm and continuously titrating $CaCl_2$ as described in Experimental Procedures. The intensity was dilution-corrected and is shown in the inset. The Hill equation (dotted curve) was fitted to the normalized intensity (rough curve).

Figure 1A:
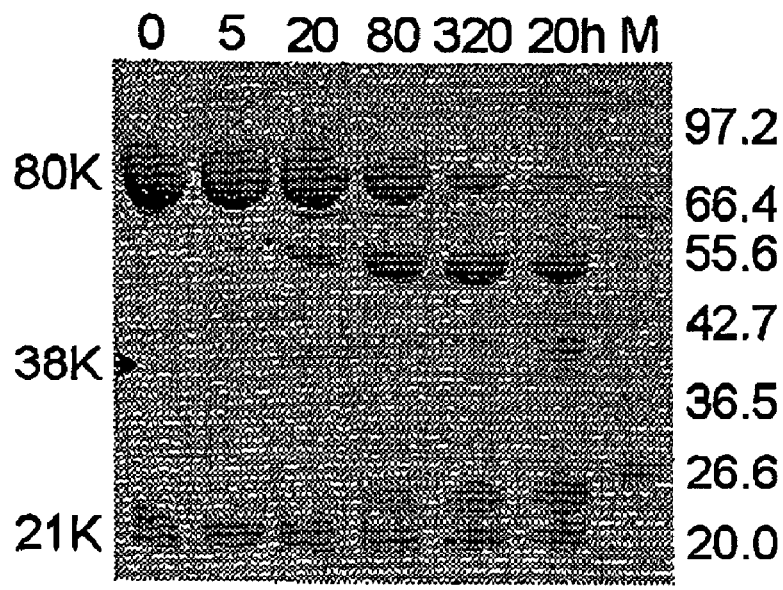
FIG. 1. Biochemical properties of μI-II suggest its role as a $Ca^{2+}$-dependent cysteine protease.
Figure 1D:
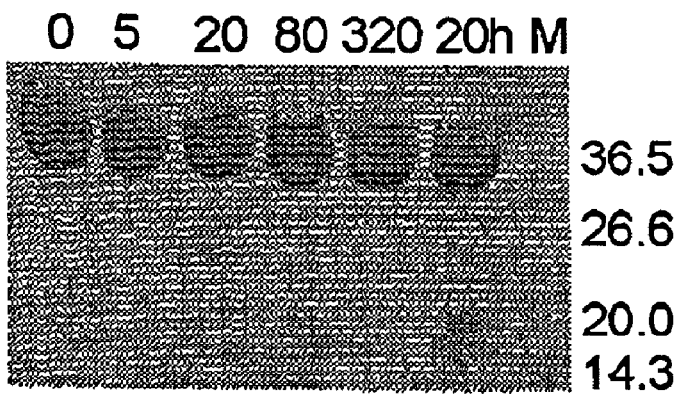
Figure 1B:
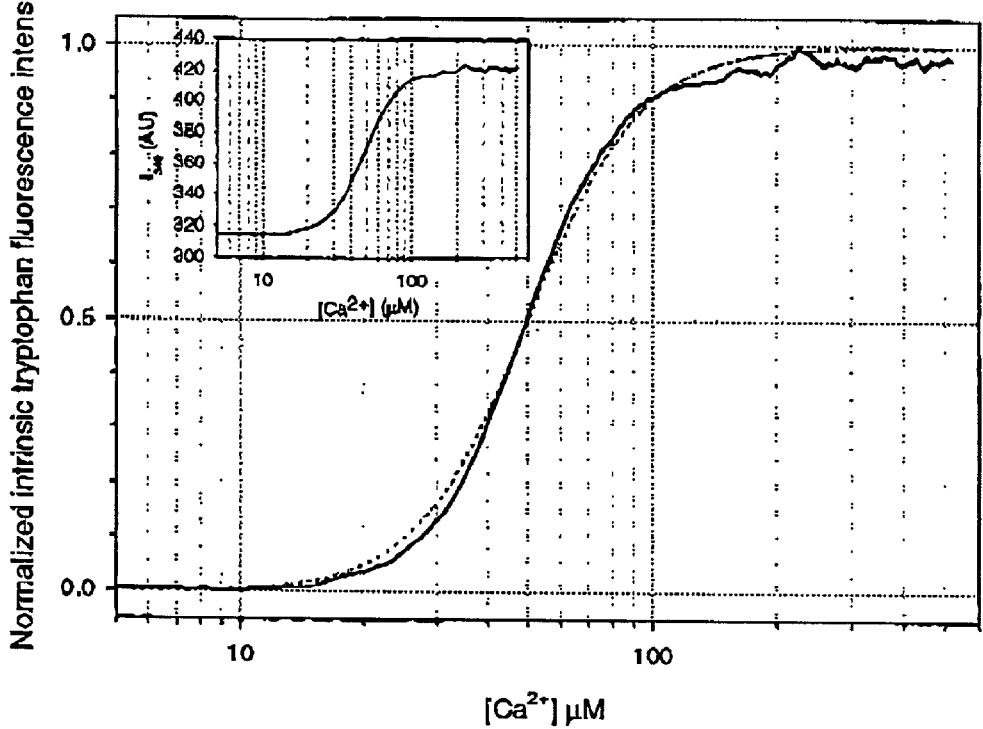

(C) The Michaelis-Menten kinetics for the proteolysis of the synthetic peptide SLY-MCA by μI-II in the presence of 0.5 mM $CaCl_2$ were obtained under the same reaction conditions as in FIG. 1B but in the presence of increasing substrate concentrations as described under Experimental Procedures.

(D) μI-II autolysis in the presence of 1 mM $CaCl_2$ was performed as the proteolysis of FIG. 1A by excluding the substrate (80K/21K) and increasing the enzyme concentration (2.5 mg/mL), and is captured by the SDS-PAGE profile.

Figure 2:
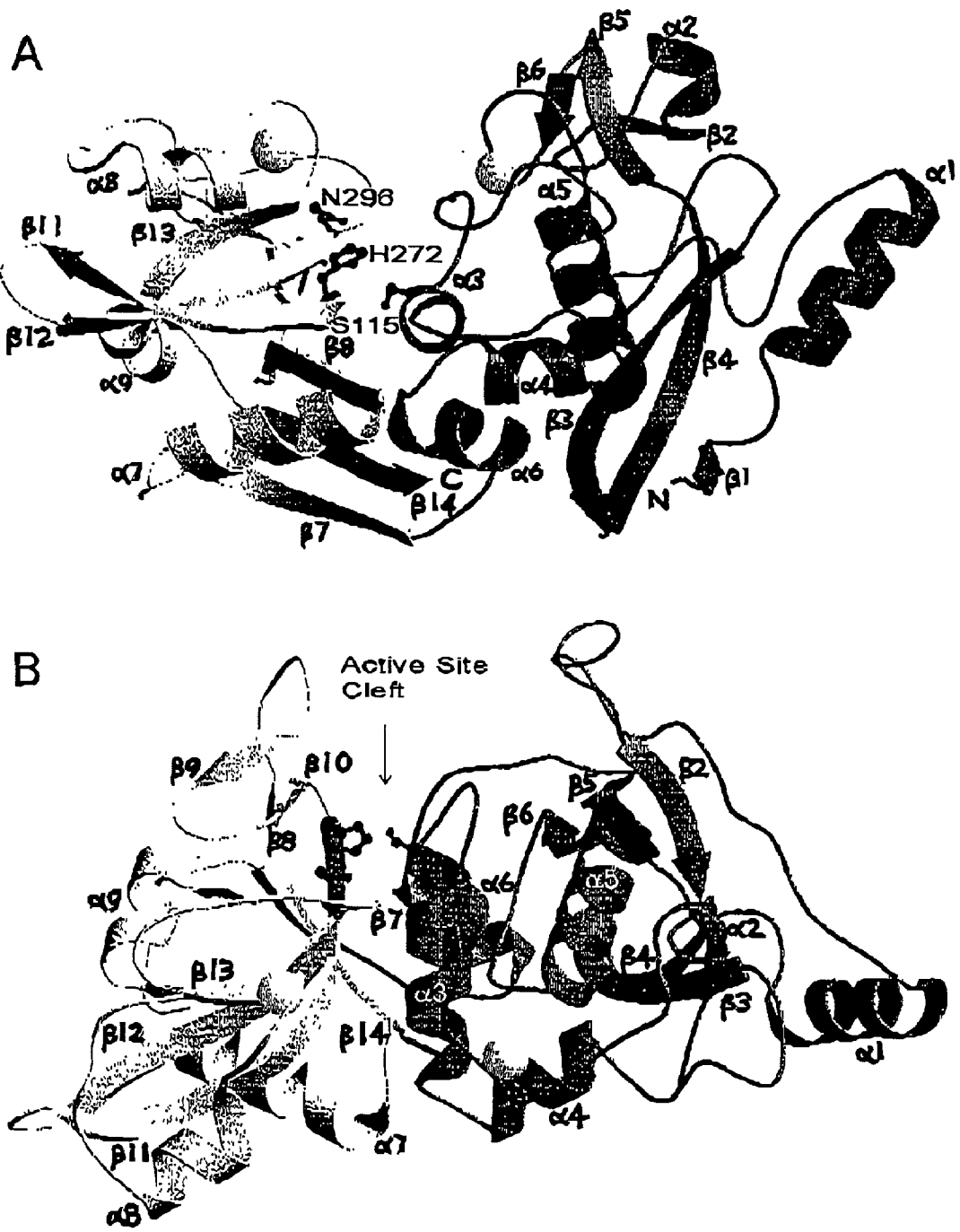

FIG. 2. The overall structure of μI-II construct.

(A) The front view of μI-II looking down α3 on which the active site cysteine residue resides. This cysteine was mutated to serine (C115S). Domain I is colored in blue whereas domain II is colored in cyan. β-strands and α-helices are numbered following the order of their appearance from the N-terminus (N) to the C-terminus (C). The gold-colored balls indicate the positions of the two calcium ions. The side chain atoms of the catalytic triad residues are colored in red (oxygen), dark blue (nitrogen), and gray (carbon) while the inter-atomic bonds are colored in gray. The figure was generated using Molscript (Kraulis, P. J., *J. Appl. Crystallogr.* 24: 946–950 (1991)).

(B) The top view, obtained by a 90° rotation along the long axis of the front view, shows the relative arrangement of the $Ca^{2+}$ ions and the active site cleft.

Figure 3:
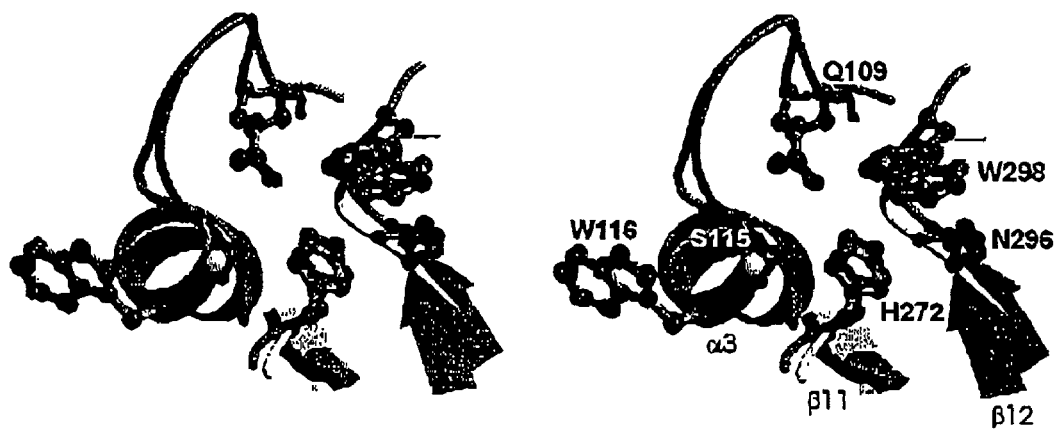

FIG. 3. Active site residues overlap between μI-II and papain. The side chains of active site residues in papain (C25, H159, N175, Q19, W177; numbers not shown) were overlapped onto the side chains from corresponding residues in μI-II (numbers shown) using the program Lsqkab (Kabsch, W., *Acta Cryst.* A32: 922–923 (1976)). A stereoview of the overlap was generated using Molscript (Kraulis, P. J., *J. Appl. Crystallogr.* 24: 946–950 (1991)). μI-II domains are colored the same as in FIG. 2. Papain secondary structure and side chain bonds are colored orchid. Atoms are colored as in FIG. 2 with the sulphur atom of the active site C25 colored yellow.

Figure 4:
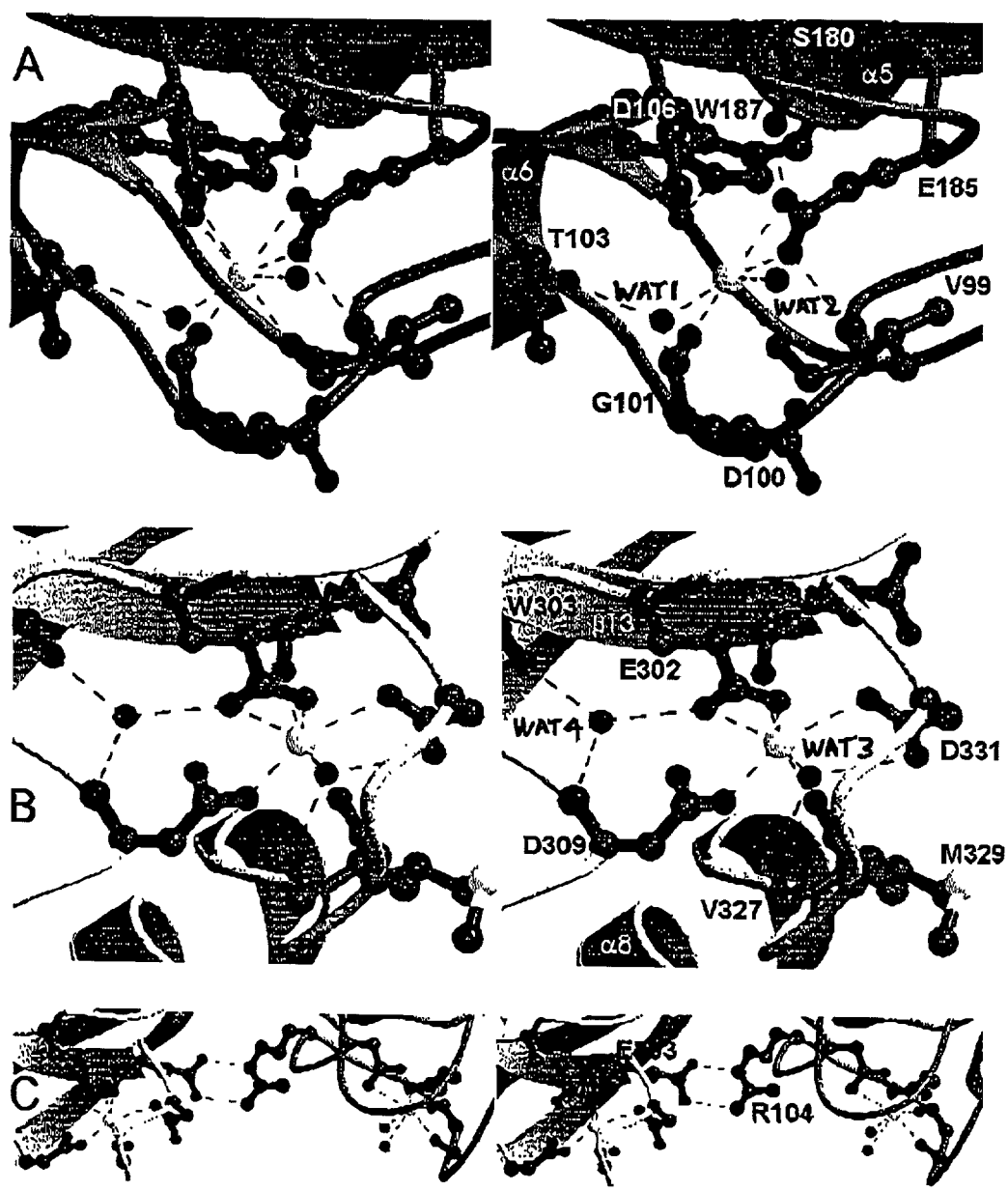

FIG. 4. Two novel cooperative $Ca^{2+}$-binding sites in the protease region of calpain (A) Domain I $Ca^{2+}$ is coordinated by eight oxygen atoms (red lines). Four coordinations are from the side chains of D106 and E185, two from the backbone carbonyl of V99 and D101, and two from water molecules WAT1 and WAT2. Black lines show stabilizing interactions to coordinating oxygen atoms.

(B) Domain II $Ca^{2+}$ site has a pentagonal bypiramid geometry with four coordinations from the side chains of E302 (2), D309 (1), and D331 (1), two backbone carbonyl coordinations from M329 and E333, and one water coordination (WAT3). This water molecule is held in place by interactions to the $O_\gamma$ of D331 and the carbonyl oxygen of V327 (black lines).

(C) The structural basis for the observed cooperativity of $Ca^{2+}$ binding includes the R104_E333 double salt bridge interaction. While R104 is flanked by domain I $Ca^{2+}$-coordinating residues V99, G101, and D106, E333 provides one of the domain II coordinating oxygens through its backbone carbonyl. The secondary structure, atoms, and bonds are colored as in FIGS. 2 and 3. The three figures were generated using Molscript (Kraulis, P. J., *J. Appl. Crystallogr.* 24: 946–950 (1991)).

Figure 5:
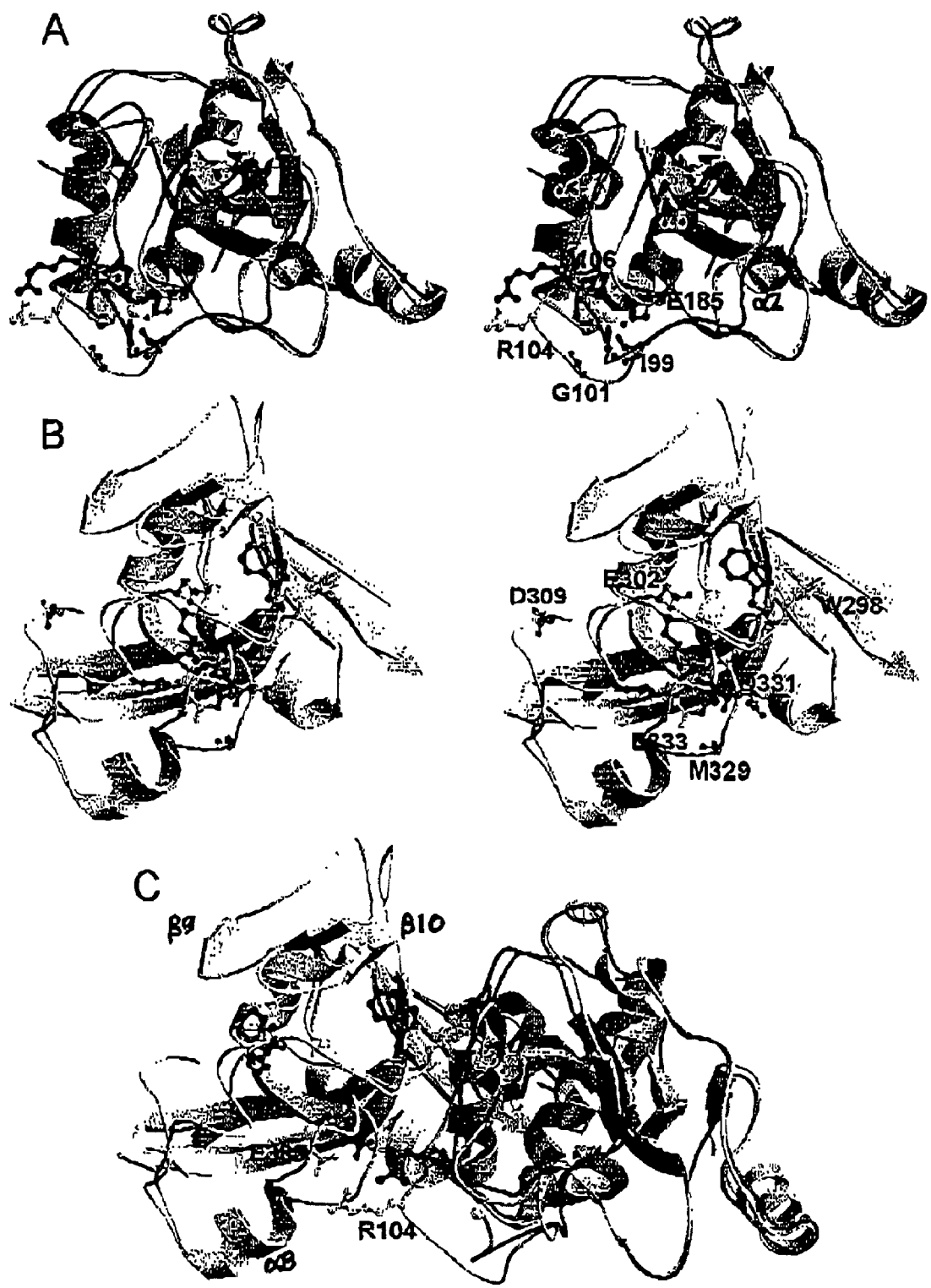

FIG. 5. $Ca^{2+}$-induced conformational changes in the active site region of calpain. Domain I and domain II of the inactive human m-calpain heterodimer (pink) were individually overlapped onto the corresponding domains of μI-II using the program align (Cohen, G. E., *J. Appl. Crystallogr.* 30: 1160–1161 (1997)). The numbering of residues differs by 10 for m- and μ-calpain due to a shorter N-terminus anchor of m-calpain. The numbering from m-calpain is used here.

(A) $Ca^{2+}$-binding to domain I results in a significant rearrangement of one loop that accommodates three of the four $Ca^{2+}$-coordinating residues. R94 is repositioned closer to domain I in place for the interaction with E323 of domain 2. Helix α2 and helix α3, which contains the active site cysteine, flank this loop and are slightly repositioned during $Ca^{2+}$ binding. E175, a residue with two side chain coordinations to the $Ca^{2+}$, does not move significantly in the presence of $Ca^{2+}$ making it a primary candidate for the $Ca^{2+}$ binding nucleation site in domain I.

(B) $Ca^{2+}$-binding to domain II results in a much more pronounced conformational change both at the level of secondary structure as well as side chain positions. The two loops with four residues that coordinate $Ca^{2+}$ move towards the $Ca^{2+}$ site, which has to be freed from steric interference from the side chain of E323. This residue rotates out of the inactive position in order to expose its backbone oxygen for coordination of the $Ca^{2+}$. The formation of an antiparallel sheet β9-β10 exposes a hydrophobic pocket that accommodates W288. None of the $Ca^{2+}$-coordinating residues in domain II are in a conformation resembling the active conformation prior to $Ca^{2+}$ binding.

(C) The overall change in conformation can be observed when the overlaps in A) and B) are merged onto the μI-II structure. In the $Ca^{2+}$-bound orientation R94 and E323 are interacting in a more buried interdomain region providing the structural basis for $Ca^{2+}$ cooperativity. W288 is pulled out from in between the domains allowing active site assembly. Another tryptophan residue that changes conformation is W293, perhaps being the second contributor to the observed change in intrinsic tryptophan fluorescence with $Ca^{2+}$.

FIG. 6 $Ca^{2+}$-dependent mechanism of activation of μI-II (A) The active site region of the human m-calpain heterodimer (pink) was overlapped onto μI-II (blue) using domain II as the overlapping criterion. The large conformational change can be easily observed by comparing domain I between the two structures. If domain II were fixed, domain I (pink) would have to be translated along helix α5 in order to bring helix α3 in the active position (blue). Moreover, a small rotation of domain I around the longitudinal axis of the active site region would have to occur to bring helix al in position. R104 and E333 are far apart in the inactive structure. $Ca^{2+}$ binds first at domain I due to the existence of an already positioned $Ca^{2+}$-coordinating residue E185 (FIG. 5), resulting in the repositioning of R104 side chain in proximity to E333 side chain.

Figure 6A:
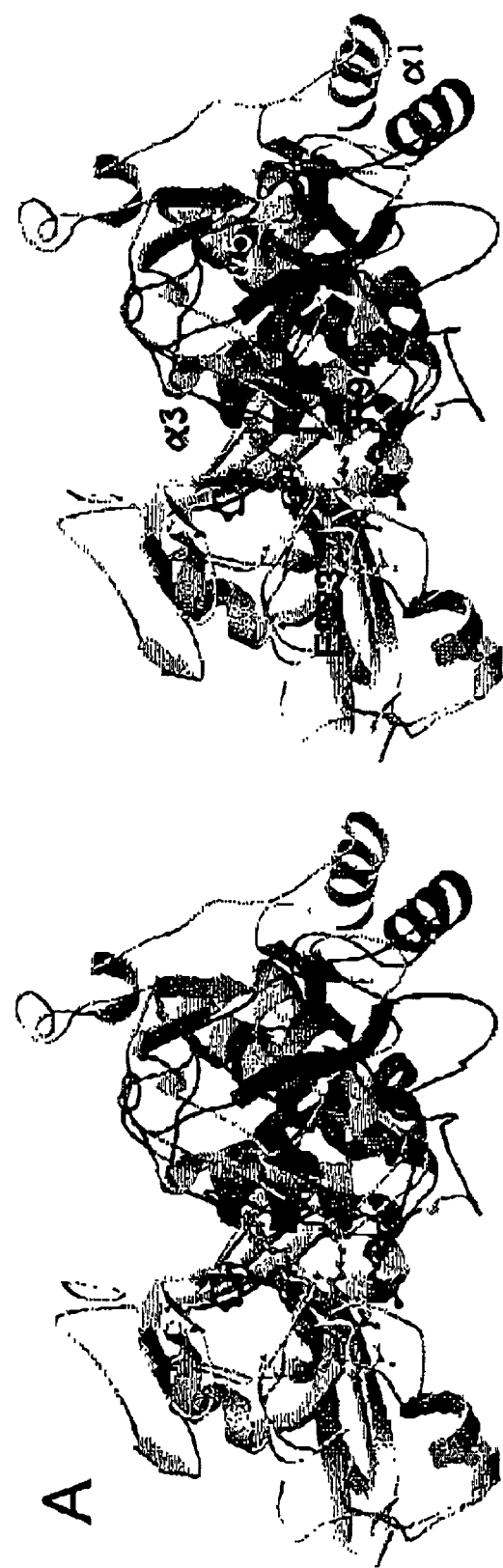

(B) R104 side chain stimulates the observed peptide flip of E333, which exposes the first $Ca^{2+}$-coordinating residue in domain II, and hence the nucleation site in domain II. As more of the $Ca^{2+}$-coordinating residues in domain II collapse onto the positioned $Ca^{2+}$, the formation of a short antiparallel sheet β9-β10 occurs on the domain II side of the active-site cleft. FIGS. 6A and B were prepared using Molscript (Kraulis, P. J., *J. Appl. Crystallogr.* 24: 946–950 (1991)).

(C) A hydrophobic pocket is formed by the side chains of residues I263 and V269 native to β9-β10, and by the neighboring V301, which accommodates W298. As this tryptophan is removed from in between the two domains more inter-domain interactions are established, stabilizing the active conformation (FIG. 6A). FIG. was generated using GRASP.

Figure 7A:
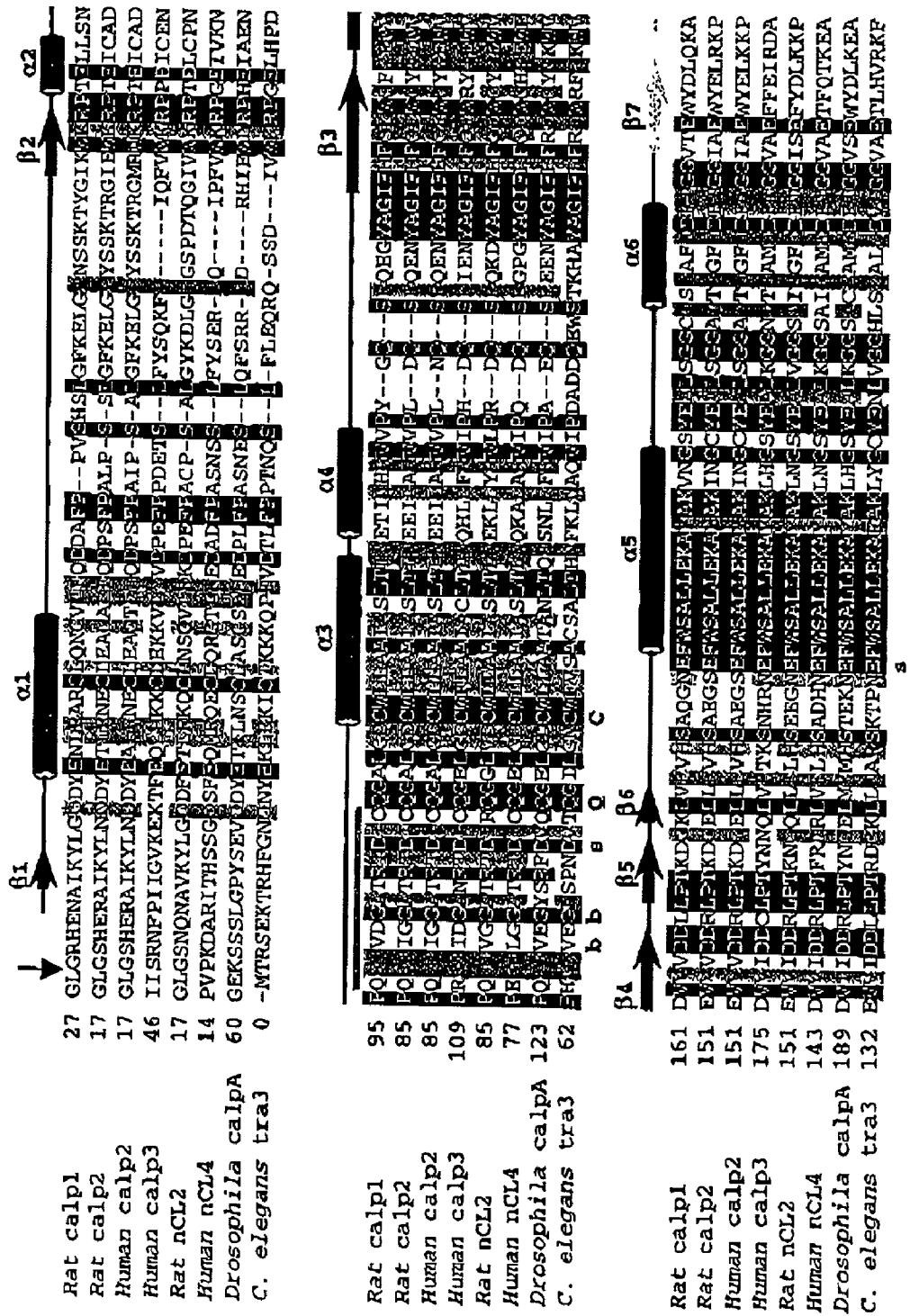
Figure 7B:
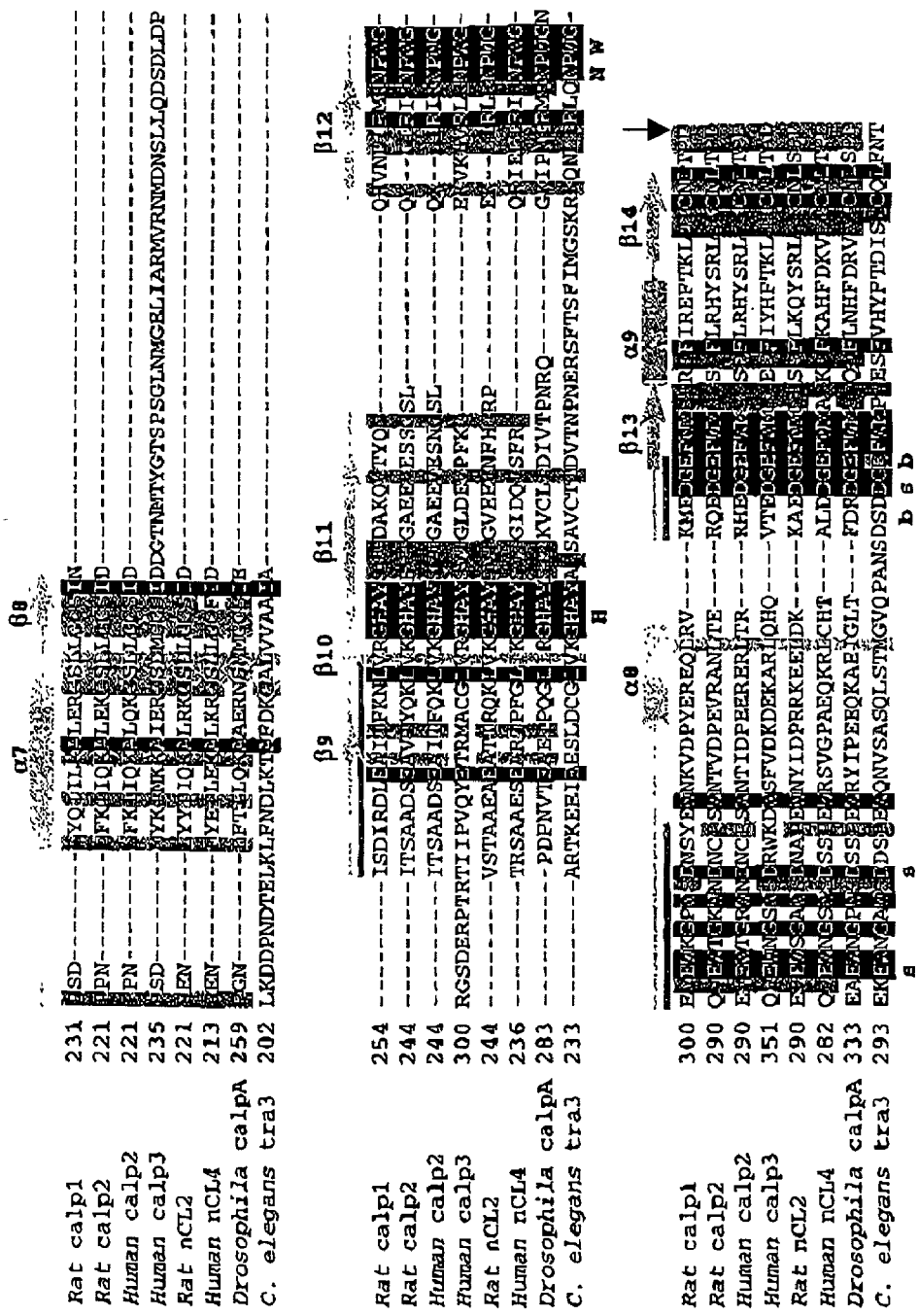

FIG. 7A and B. Distantly related calpain large subunit homologues have conserved $Ca^{2+}$-binding determinants. The sequence of the protease region of μI-II (delimited by black arrows) was aligned using clustalW (http://searchlauncher.bcm.tmc.edu:9331/multi-align/Options/clustalw.html), with the corresponding region from seven isoforms. The identity level between this isoforms is indicated in black, green, and yellow, corresponding to 100%, =75%, =50% identity, respectively. All the residues that coordinate $Ca^{2+}$ through their side chain are identical in all these calpains (red highlight; red, bottom s). Most of the backbone coordinations are highly conserved even though the requirement for conservation is not as stringent at these positions (red, bottom b). Seven of the eight isoforms have the conserved R104, which presumably interacts as seen in μI-II with E333 (blue, highlights). The *C. elegans* tra3 is an exception suggesting a different mechanism of cooperativity between the $Ca^{2+}$ sites. Catalytic residues are shown in bold below the alignment. Above the alignment the secondary structure elements are shown with the sheets and helices numbered and colored as in FIG. 2. The pink bars correspond to regions that have a different conformation in the inactive human m-calpain heterodimer as seen in FIG. 5. Accession numbers for these isoforms are: rat calp1 (μ) NP_062025.1, rat calp2 (m) AAA16327.1, human calp2 A31218, human calp3 (p94) A56218, rat nCL2 A48764, human nCL4 XP_001445.1, *D. melanogaster* calpA CAA55297.1, *C. elegans* tra3 S71885.

Figure 8:
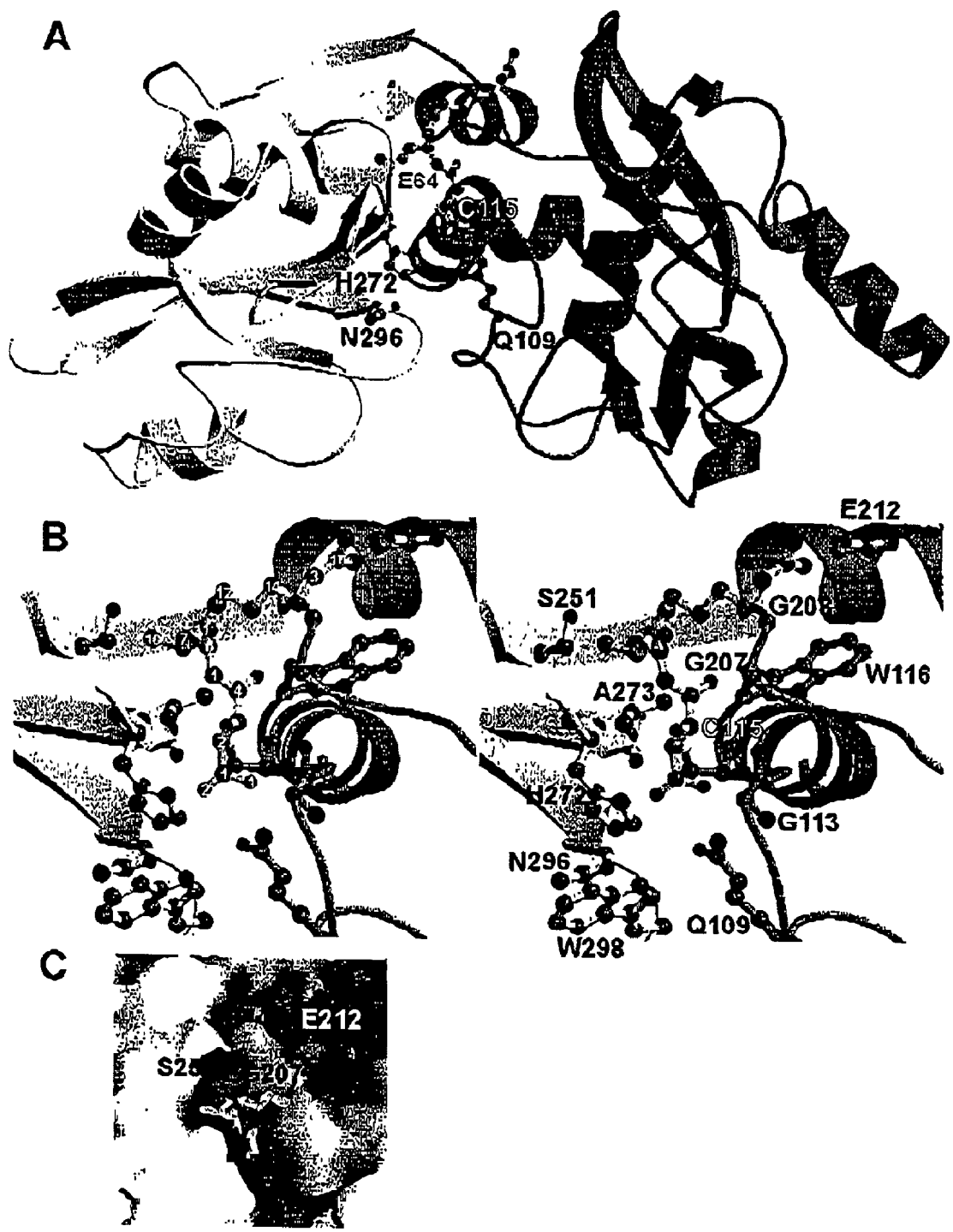

FIG. 8. Mode of binding of E64 to calpain.

(A) Overall view of mul-II-E64 showing E64 (green bonds) bound across the P sites in the active site cleft. DI and II and their side chain bonds are colored blue and cyan, respectively. Oxygen, sulphur, nitrogen, and carbon atoms are colored red, yellow, blue, and grey, respectively.

(B) Stereoview showing a close-up of the interactions made by E64 at the active site cleft of calpain. E64 ($C_{15}N_5O_5$) atom numbering is indicated at several positions along the molecule. Carbon 5 position was historically omitted such that the last carbon is $C_{16}$.

(C) GRASP potential over molecular surface representation of the active site close-up seen in (B) showing E64 complexed. The P' site interaction including the covalent link to the active site thiol (E64-$C_2$-Sγ) is buried. Red, blue, and white represent electronegative, electropositive and neutral potential energy, respectively.

DETAILED DESCRIPTION OF THE INVENTION

Introduction

The present invention provides a method for crystallizing one or more domains of cation-dependent (and preferably calcium-dependent) polypeptides in the presence of the cation, where the crystals diffract at a sufficiently high resolution to allow determination of a model of the crystal structure. The term "calcium" refers to all forms and states of the element, including but not limited to ionic, non-ionic and complexed. In one such embodiment the domain is a ligand binding domain (LBD). In a highly preferred embodiment, the domain is the ligand binding domain of an enzyme, such as calpain. The present invention further provides a computer readable medium having stored thereon a model of the domain crystal structure. By the invention, a model of the domain crystal structure can be used in a computer-based system for the identification or rational design of ligands interacting with the domain, if the domain is a LBD. Such ligands can be synthesized chemically according to known techniques. In a preferred embodiment, the identified ligands induce a conformational change in the cation-binding polypeptide. Such ligands can act as inhibitors, activators or substrates of the polypeptide.

The model of the domain crystal structure can be determined using the amino acid sequence of the domain of interest and X-ray diffraction data obtained from the crystals. A computer analysis of these data allows the determination of the secondary, tertiary and quaternary structures of the domain.

Isolation and Purification of Polypeptide Domains

The invention as provided herein utilizes certain methods and techniques that are well-known to those skilled in the relevant arts. Methods and techniques for the growth of bacterial cells, the introduction of isolated DNA molecules into host cells, and the isolation, cloning and sequencing of isolated nucleic acid molecules, etc., are a few examples of such methods and techniques. These methods and techniques are described in many standard laboratory manuals, such as Davis et al., *Basic Methods In Molecular Biology* (1986), J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E. F. Fritsch and T. Maniatis, *Molecular *Cloning: A Laboratory Manual,* 2d ed., Cold Spring Harbor Laboratory Press, Cold Spring Harbor, N.Y. (1989); P. B. Kaufman et al., *Handbook of Molecular and Cellular Methods in Biology and Medicine,* CRC Press, Boca Raton, Fla. (1995); *Methods in Plant Molecular Biology and Biotechnology,* B. R. Glick and J. E. Thompson, eds., CRC Press, Boca Raton, Fla. (1993); and P. F. Smith-Keary, *Molecular Genetics of Escherichia coli,* The Guilford Press, New York, N.Y. (1989), all of which are incorporated herein by reference in their entireties.

cDNA clones comprising a nucleic acid molecule encoding the polypeptide domain of interest can be isolated from a library by standard molecular biology techniques, such as hybridization and screening or amplification using polymerase chain reaction. cDNA inserts can then be subcloned into an appropriate vector and sequenced for confirmation.

The domains of interest in the cation-dependent (and preferably calcium-dependent) polypeptide can be determined by a variety of methods. Important functional or structural domains are often conserved during evolution. Analysis of related polypeptides from various species can detect such conserved domains. Such analysis is referred herein as "evolutionary conservation analysis."

It is also possible to ascertain functionally important domains by expressing truncated versions of the polypeptide, and analyzing the resulting truncated polypeptides for functional or structural integrity. For example, a truncated polypeptide may be a polypeptide beginning with amino acids (aa) 2, 3, 5, 10, 15 or 50 of the native polypeptide. Such analysis is referred herein as "truncation analysis." Limited proteolysis can be used to map structurally stable domains that are then much easier to crystallize in order to establish their structure and/or function.

It is also possible to ascertain functionally important domains by mutating residues along the polypeptide and analyzing the function of the resulting mutants, looking for mutations that abolish the function of the polypeptide. Mutations are introduced into the nucleic acid sequence (typically cDNA) encoding the polypeptide. Mutations can be introduced into the nucleic acid sequence by techniques well-known to those skilled in the art. One such technique is polymerase chain reaction. Mutated nucleic acid sequences are subcloned into expression vectors (as will be described below), and expressed in an appropriate host. The mutated polypeptides are then tested for structural and/or functional changes as compared to the native, non-mutated polypeptide. Such analysis is referred herein as "mutation analysis."

Such nucleic acid molecules which encode the polypeptide domain, preferably in the form of cDNA, can be recombined with vector DNA in accordance with conventional techniques, including using blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are well known, e.g., as disclosed in Sambrook et al., *Molecular Cloning: A Laboratory Manual,* Second edition, Cold Spring Harbor Laboratory, Cold Spring Harbor, N.Y. (1989); and Ausubel et al., *Current Protocols in Molecular Biology,* Wiley Interscience, N.Y. (1988–1995).

A nucleic acid molecule, such as a cDNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression of a polypeptide comprising the domain of interest in recoverable amounts. The precise nature of the regulatory regions needed for gene expression can vary from organism to organism, as is well known in the art. See, e.g., Sambrook, *Molecular Cloning: A Laboratory Manual,* Second edition, Cold Spring Harbor Laboratory, Cold Spring Harbor, N.Y. (1989); and Ausubel et al., *Current Protocols in Molecular Biology,* Wiley Interscience, N.Y. (1988–1995).

The invention accordingly encompasses the expression of a polypeptide containing the domain of interest, or a mutant fragment, variant or derivative thereof, in prokaryotic and eukaryotic cells. Preferred hosts include *E. coli,* Bacillus species, yeast, insects, fungi, bird and mammalian cells either in vivo or in situ.

For introduction of nucleic acid molecules encoding polypeptide domains of interest into a host cell, a great variety of vectors can be used in the invention. Such vectors include chromosomal, episomal and virus-derived vectors, e.g., vectors derived from bacterial plasmids and from bacteriophage, as well as vectors derived from combinations thereof, such as those derived from plasmid and bacteriophage genetic elements, such as cosmids and phagemids, all may be used in accordance with this aspect of the present invention. Retroviral vectors may be replication competent or replication defective. In the latter case, viral propagation generally will occur only in complementing host cells. Preferred for use in the present method are vectors suitable to maintain and propagate a polynucleotide in a bacterial host.

A large number of suitable vectors and promoters for use in bacteria are known, many of which are commercially available. Preferred prokaryotic vectors include plasmids such as those capable of replication in *E. coli* (such as pBR322, ColE1, pSC101, pACYC 184, πVX). Such plasmids are, for example, disclosed by Maniatis, T., et al., *In: Molecular Cloning,* A Laboratory Manual, Cold Spring Harbor Press, Cold Spring Harbor, N.Y. (1982)). The following vectors may be used by way of example: pET (Novagen), pQE70, pQE60, pQE-9 (Qiagen), pBs, phagescript, psiX174, pBlueScript SK, pBsKS, pNH8a, pNH16a, pNH18a, pNH46a (Stratagene), pTrc99A, pKK223-3, pKK233-3, pDR540, pRIT5 (Pharmacia). The selected vector is preferably capable of being induced to over-express the domain of interest.

Once the vector or nucleic acid molecule containing the construct(s) has been prepared for expression, the DNA construct(s) can be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells and expression of the polypeptide or one or more domains thereof.

The polypeptide domain, expressed by the means described above, can be isolated and purified in accordance with conventional method steps, such as extraction, precipitation, chromatography, affinity chromatography, electrophoresis, or the like, according to methods of protein isolation that are well known in the art. For example, cells expressing at least one polypeptide domain in suitable levels can be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation. Alternatively, the polypeptide domain can be isolated by the use of immunoaffinity, using antibodies directed against the polypeptide or domain(s) of interest. Such antibodies can be obtained by known method steps (see, e.g., Harlow and Lane, *ANTIBODIES. A LABORATORY MANUAL*, Cold Spring Harbor Laboratory (1988); Colligan et al., eds., *Current Protocols in Immunology*, Greene Publishing Assoc. and Wiley Interscience, N.Y., (1992, 1993)). The nucleic acid molecule encoding the domain of interest can also be cloned in tandem with a nucleic acid encoding a histidine-"tag" (a variable number of his amino acids at the N- or C-termini), resulting in a fusion protein. The resultant protein can be purified by an anti-His antibody column or by metal chelate affinity chromatography and gel filtration. Other tags include GST, β-gal, epitopes MBP, HA, i.e., any molecule or part of a molecule known in the art that will interact specifically and reversibly with a column matrix or antibody. Optionally, such tags are removed after the purification of the fusion protein by, for example, protease digestion leaving only the native domain of interest.

Alternatively, peptide sequences corresponding to the domains of interest may be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, J. Am. Chem. Soc. 88:2149 (1963); Meienhofer, Hormonal Proteins and Peptides, C. H. Li, Ed., Academic Press, 1983, pp. 48–267; and Barany and Merrifield, in The Peptides, E. Gross and J. Meienhofer, Eds., Academic Press, New York, 1980, pp.3–285. Methods of solid phase peptide synthesis are described in Merrifield, R. B., Science, 232: 341 (1986); Carpino, L. A. and Han, G. Y., J. Org. Chem., 37: 3404 (1972); and Gauspohl, H. et al., Synthesis, 5:315 (1992)). The teachings of these references are incorporated herein by reference.

In general, the domain of the cation-dependent (and preferably calcium-dependent) polypeptide is preferably isolated in soluble form in sufficient purity and concentrated for crystallization. The domain can then be assayed for lack of aggregation (which interferes with crystallization) in the presence of the cation with which it will be crystallized. The purified domain, in the presence of the selected cation, is preferably crystallized under varying conditions (including those described in detail below and in the Examples) of at least one of the following: pH, buffer type, buffer concentration, salt type, polymer type, polymer concentration, other precipitating ligands and concentration of purified domain polypeptide. See, e.g., Blundell et al., *Protein Crystallography*, Academic Press, London (1976); McPherson, *The Preparation and Analysis of Protein Crystals*, Wiley Interscience, N.Y. (1982). The crystallized domain can optionally be tested for native cation-dependent (and preferably calcium-dependent) polypeptide activity and differently sized and shaped crystals are further tested for suitability for X-ray diffraction. Generally, larger crystals provide better crystallographic data than smaller crystals, and thicker crystals provide better crystallographic data than thinner crystals.

Any suitable crystallization method can be used for crystallizing the domain of interest, such as the hanging-drop vapor diffusion method, microbatch, sitting drop and dialysis. Preferably, crystallizing will occur at a temperature of about 10–20° C. The crystals should be grown in the presence of a cation (and optionally in the presence of a ligand) for 1–14 days (preferably 4–5 days) from a solution containing one or more of the following: sodium acetate, Pipes, NaCl, Tris/HCl, DTT, C12M, CHAPS, MES, HEPES, PEG 6000 and glycerol (preferably, about 0.5 to 2 M sodium chloride, about 0.5 to 4% PEG 6000, about 0.02 to 0.2 M MES pH 5.0–7.0, about 2 to 20% glycerol, about 2 to 20 mM HEPES, about 2 to 20 mM DTT and about 2 to 20 mM calcium chloride.). However, it will be understood in the art that any appropriate agent buffering at about pH 5.0–7.0 can be used.

Crystals grown according to the present invention preferably diffract X-rays to at least 10 Å resolution, such as 0.5–10.0 Å, or any range of value therein, such as 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4 or 3.5, with 3.5 Å or higher being preferred for determining the crystal structure. However, diffraction patterns with a lower resolution, such as 2.5–3.5 Å, are also useful.

According to the present invention, during growth, some of the crystals can be optionally removed, washed, and assayed for biological activity. Other washed crystals can be run on a gel and stained, and those that migrate at the same molecular weight as the corresponding purified polypeptide domain are preferably used. From one to two hundred crystals can be observed in one drop. Useful crystal forms which occur are tetragonal. Initial X-ray analyses indicate that such crystals diffract at moderately high to high resolution. When fewer crystals are produced in a drop, they can be a much larger size.

Heavy atom derivatives used for multiple isomorphous replacement (as discussed below) can be obtained by either soaking the crystals with a mercurial reagent (e.g., sodium para-chloromercuribenzylsulphonate (PCMBS) 0.5 mM, 2 h or 0.1 mM, 24 h) or placing crystals in a gaseous xenon (Xe) atmosphere prior to data collection (Schiltz et al., *J. Appl. Cryst.* 27: 950–960 (1994)).

X-ray Crystallography

In a preferred aspect of the invention, crystals produced according to the present methods are preferably analyzed using a suitable X-ray source to obtain diffraction patterns. Preferably, crystals are used which are stable for at least 10 h in the X-ray beam. Frozen crystals (e.g., −220 to −50° C.) are optionally used for longer X-ray exposures (e.g., 5–72 h), the crystals being relatively more stable to the X-rays in the frozen state. To collect the maximum number of useful reflections, multiple frames should be collected as the crystal is rotated in the X-ray beam. Larger crystals (>150 μm) are preferred to increase the resolution of the X-ray diffraction patterns obtained. Crystals are preferably analyzed using a synchrotron high energy X-ray source. Using frozen crystals, X-ray diffraction data is collected on crystals that diffract to at least a relatively high resolution of 10–1.5 Å, with lower resolutions also being useful, such as 25–10 Å, sufficient to solve the three-dimensional structure of the domain of interest.

Passing an X-ray beam through a crystal produces a diffraction pattern as a result of the X-rays interacting and being scattered by the contents of the crystal. The diffraction pattern can be visualized using, e.g., an image plate or film, resulting in an image with spots corresponding to the diffracted X-rays. The positions of the spots in the diffraction pattern are used to determine parameters intrinsic to the crystal (such as unicell parameters) and to gain information on the packing of the molecules in the crystal. The intensity of the spots contains the Fourier transformation of the molecules in the crystal, i.e., information on each atom in the crystal and hence of the crystallized molecule.

After data collection of diffraction patterns, the data are processed. For example, in the studies described below, X-ray data were collected at about 0° C. using either a MarResearch imaging plate detector or a Siemens area detector mounted on a rotating-anode generator ($\lambda$=1.54 Å) and at about −5° C. on the W32 beamline of the LURE synchrotron (Laboratoire pour l'Utilisation du Rayonnement Electromagnétique, Orsay, France; $\lambda$=0.98 Å). Data were processed using the MarXDS package Kabsch, W. *J. Appl. Crystallogr.* 21:916–924(1988)). The MarXDS package is a Fortran program developed for the reduction of single-crystal diffraction data from a sequence of adjacent rotation pictures recorded at a fixed X-ray wavelength by an electronic area detector. Patterson and cross Fourier analyses and SIR phasing can be done using programs from the CCP4 package (Collaborative Computational Project No. 4, *Acta Cryst.* D50:760–763 (1994)), which is a suite of programs for the reduction and analysis of intensity data, structure solution by isomorphous replacement and molecular replacement, least-squares refinement, analysis of the structure, displaying electron-density maps and plotting molecules. Of course, other methods of data collection and analysis familiar to those of ordinary skill in the art may also be used in accordance with the invention.

In general, X-ray diffraction data processing includes measuring the spots on each diffraction pattern in terms of position and intensity. This information is processed as indicated above (i.e., mathematical operations are performed on the data (such as scaling, merging and converting the data from intensity of diffracted beams to amplitudes)) to yield a set of data which is in a form as can be used for the further structure determination of the molecule. The amplitudes of the diffracted X-rays are then combined with calculated phases to produce an electron density map of the contents of the crystal. In the electron density map, the structure of the molecules (as present in the crystal) is built. The phases can be determined with various known techniques, one being molecular replacement.

For the molecular replacement technique, a known three dimensional structure thought to share structural homology with the structure to be determined, is used to generate, after calculations, a first set of initial phases. These phases can be combined with the diffraction information of the molecule being structurally analyzed.

The phases can be further optimized using a technique called density modification, which allows electron density maps of better quality to be produced facilitating interpretation and model building therein. The model is then refined by allowing the atoms in the model to move in order to match the diffraction data as well as possible while continuing to satisfy stereochemical constraints (sensible bond lengths, bond angles and the like).

Structure Determination

Overview. By the invention, the X-ray diffraction patterns obtained from a crystal produced as described above can be analyzed directly to provide a model of the three dimensional structure of the domain of interest. As indicated, when provided on computer readable media, the X-ray diffraction patterns can be used to generate electron density maps. Although the diffraction patterns are usually themselves sufficient for three-dimensional structure determination, the amino acid sequence of the domain of interest is also useful. The electron density maps, provided by analysis of the X-ray diffraction patterns, are then fitted using suitable computer algorithms as described below to generate secondary, tertiary and/or quaternary structure of the domain of interest providing an overall three-dimensional model.

Map Interpretation. Electron density maps can be calculated using such programs as those from the CCP4 computing package described above. Cycles of two-fold averaging can further be used, such as with the program RAVE (Kleywegt & Jones, Bailey et al., eds., *First Map to Final Model*, SERC Daresbury Laboratory, UK, pp.59–66 (1994)) and gradual model expansion. The interpretation of electron density maps phased by multiple isomorphous replacement (MIR) to produce an initial molecular model is a critical step during the model building process. Three-dimensional computer graphics workstations are now widely used in the art for constructing models in MIR maps. One computer program in particular, FRODO, is commonly used and is available on a range of workstations (Jones, T. A., *J. Appl. Cryst.* 11:268–272 (1978)). In an attempt to improve the ability to interpret maps and then to construct more accurate models, Jones & Thirup, *EMBO J* 5:819–822 (1986), introduced the use of skeletons coupled with a protein database of the best refined protein structures to build the initial model. This work suggested that all protein models could be built from fragments of existing structures. Jones et al. (Jones et al., *Acta Cryst.* A47:110–119 (1991)), extended these ideas with a computer graphics program called "O," which allows the user to go from an initial $C\alpha$ trace to a well refined model without manual intervention. An overview of one strategy used is provided below:

Map
Calculate Skeletonized Map
Edit Skeletonized Map
Assign $C\alpha$ positions from skeleton
Autobuild Main Chain
Autobuild Side Chain
RSR_rotamer each residue
RSR_rigid each residue
Restore Stereochemistry
Crystallographic Refinement Refinement and Model Validation. Rigid body and positional refinement can be carried out using a program such as CNS (Brünger, A. T., *Acta Cryst.* D45: 905–921 (1998)) to a suitable crystallographic $R_{factor}$. If the model at this stage in the averaged maps still misses residues (e.g., at least 5–10 per subunit), then some or all of the missing residues can be incorporated in the model during additional cycles of positional refinement and model building. The refinement procedure can start using data from lower resolution (e.g., 25–10 Å to 10–3.0 Å) and then gradually be extended to include data from 12–6 Å to 3.0–1.5 Å. B-values (also termed temperature factors) for individual atoms can be refined once data of 2.8Å or higher (e.g., up to 1.5 Å) has been added. Subsequently waters can be gradually added. A program such as ARP (Lamzin and Wilson, *Acta Cryst.* D49:129–147 (1993)) can be used to add crystallographic waters and as a tool to check for bad areas in the model. Programs such as PROCHECK (Lackowski et al., *J. Appl. Cryst.* 26:283–291 (1993)), WHAT IF (Vriend, *J. Mol. Graph.* 8:52–56 (1990)) and PROFILE 3D (Lüthy et al., *Nature* 356:83–85 (1992)), as well as the geometrical analysis generated by CNS can be been used to check the structure for errors. A program such as DSSP can be used to assign the secondary structure elements (Kabsch and Sander, *Biopolymers* 22:2577–2637(1983)). The model data is then saved on computer readable media for use in further analysis, such as, for example, in a method for aligning the amino acid sequences of domains of other cation-dependent (and preferably calcium-dependent) polypeptides, in a method for modeling the ligand binding domains of these polypeptides, and in a computer-based system for the rational design of ligands capable of binding to ligand-binding domains of cation-dependent (and preferably calcium-dependent) polypeptides. The ligands designed by such a method can be tested for binding to the LBD of a cation-dependent (and preferably calcium-dependent) polypeptide by methods that are well known in the art. For example, ligand binding to the LBD can be quantified by the reduction in intrinsic tryptophan fluorescence.

In one embodiment, it is contemplated that the ligands that bind the LBDs of the cation-dependent (and preferably calcium-dependent) polypeptides can induce structural (e.g. conformational) changes in the polypeptide, or one or more domains thereof, upon binding to the LBDs. In another embodiment, these ligands can modulate the activity of the cation-binding polypeptide. In one such embodiment, the ligand inhibits or reduces the activity of the cation-binding polypeptide. In another such embodiment, ligand binding activates or enhances the activity of the polypeptide. In other embodiments, the ligand maybe substrate for the polypeptide. In a preferred embodiment the ligand binds to ligand-binding domains of a cation-dependent (and preferably calcium-dependent) polypeptide, which is an enzyme active site. In additional preferred embodiments, the enzyme is a protease, a nucleic acid polymerase, a transferase, a phosphatase or a kinase. In a particularly preferred such embodiment, the enzyme may be a $Ca^{2+}$-dependent protease such as calpain or an isoform thereof, particularly, m-calpain or μ-calpain, or a mutant, variant or derivative thereof. It is contemplated that the ligand thus designed, or a potential ligand discovered by any other means, can be co-crystallized with the domain of interest of the cation-dependent (and preferably calcium-dependent) polypeptide by the methods described above.

Ligand Uses

Ligands identified and/or designed according to the present methods may be used for a variety of purposes. For example, the invention provides a method of treating a disease or a physical disorder in an animal suffering from or predisposed to such a disease or physical disorder, by administering to the animal an effective amount of a ligand designed and/or identified by the methods of the present invention. The disorders that can be treated or prevented by such methods of the invention include, but are not limited to, cardiovascular disorder (such as stroke, myocardial infarction, heart disease and the like) Alzheimer's disease and other disorders that involve cation-dependent (and preferably calcium-dependent) polypeptides or enzymes. In a preferred embodiment, the animal to be treated is a mammal, most preferably a human.

It is contemplated that the ligand can be administered in pure form, or in a composition comprising a therapeutically effective amount of the ligand and a pharmaceutically acceptable excipient or carrier. By "pharmaceutically acceptable carrier" is meant a non-toxic solid, semisolid or liquid filler, diluent, encapsulating material or formulation auxiliary of any type. Such a carrier includes but is not limited to saline, buffered saline, dextrose, water, glycerol, ethanol, and combinations thereof. The formation should suit the mode of administration.

Generally, the formulations are prepared by contacting the ligand uniformly and intimately with liquid carriers or finely divided solid carriers or both. Then, if necessary, the product is shaped into the desired formulation. In one embodiment, the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g. polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

Pharmaceutical compositions containing the ligand of the invention can be administered orally, rectally, parenterally, intrasystemically, intravenously, intracraneally, intramuscularly, intravaginally, intraperitoneally, topically (as by powders, ointments, drops or transdermal patch), bucally, or as an oral or nasal spray. The pharmaceutical compositions are administered in the amount which is effective for treating and/or prophylaxis of the specific indication.

For parenteral administration, in one embodiment, the ligand is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to a polypeptide.

The ligand is also suitably administered by sustained-release systems. Suitable examples of sustained-release compositions include semi-permeable polymer matrices in the form of shaped articles, e.g. films, or mirocapsules. Sustained-release matrices include polylactides (U.S. Pat. No. 3,773,919; EP 0 058 481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 0 133 988). Sustained-release ligand compositions also include liposomally entrapped Ck beta-11 and/or LAI-1 polypeptide. Liposomes containing the ligand are prepared by methods known per se: DE 3,218,121; Epstein et al., *Proc. Natl. Acad Sci. (USA)* 82:3688–3692 (1985); Hwang et al., *Proc. Natl. Acad Sci. (USA)* 77:4030–4034 (1980); EP 0 052 322; EP 0 036 676; EP 0 088 046; EP 0 143 949; EP 0 142 641; Japanese Pat. Appl. 83-118008; U.S. Pat. Nos. 4,485,045 and 4,544,545; and EP 0 102 324. Ordinarily, the liposomes are of the small (about 200–800 Angstroms) unilamellar type in which the lipid content is greater than about 30 mol. percent cholesterol, the selected proportion being adjusted for the optimal therapy.

It will be readily apparent to one of ordinary skill in the relevant arts that other suitable modifications and adaptations to the methods and applications described herein are obvious and maybe made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Determination of a $Ca^{2+}$-bound Active Site Structure of Calpain

We have shown an evolutionarily conserved novel mechanism of calpain regulation by $Ca^{2+}$. We have generated a structural entity containing the active site region of μ-calpain, which maintains the minimal requirements of a $Ca^{2+}$ dependent cysteine protease. $Ca^{2+}$-binds in a cooperative manner at two unique sites, one in each domain, resulting in a major conformational change that correlates with activation. The consequence of this conformational change is active site assembly with the catalytic residues arrangement closely resembling that of papain, as captured in the 2.1 Å crystal structure of μI-II. This structure supports the observed cooperativity between the $Ca^{2+}$ sites suggesting a mechanism for activation of this protease. Our study provides the grounds for $Ca^{2+}$ regulation of the large subunit homologues of the calpain super family. Moreover, the $Ca^{2+}$-bound structure is a perfect template for active site-directed inhibitor design. Furthermore, the physiological and pathological implications of an autolysis fragment resembling our construct add another level of regulation to the calpain system.

The protease region, composed of domains I and II, of μ-calpain was produced in high yields in *E. coli*. This construct was completely inactive in the absence of $Ca^{2+}$, but when μM levels of the divalent cation were administered, protease activity was induced. We tested the ability of μI-II to digest both a protein substrate as well as a small peptide substrate. When the inactive m-calpain heterodimer was used as substrate, a gradual digestion of the large subunit was observed which generated the diagnostic autolytic fragment fingerprint of the m-calpain heterodimer, but at a much slower rate. The slower rate was confirmed from the steady-state parameters for the digestion of the synthetic peptide SLY-MCA, being mainly due to a lower $k_{cat}$. In spite of ~2% catalytic efficiency relative to the full enzyme, the active site construct could generate very similar cleavages in the large subunit of calpain as m-calpain autolysis (Crawford, C., et al., *Biochem. J.* 296(Pt 1): 135–142 (1993); Nishimura, T., and Goll, D. E., *J. Biol. Chem.* 266: 11842–11850 (1991)), or proteolysis of intact m- by μ-calpain (Tompa, P., et al., *J. Biol. Chem.* 271: 33161–33164 (1996)). Moreover, cysteine protease specific active site inhibitors such as the reversible inhibitors leupeptin and calpain inhibitor I as well as the covalent inhibitor E64 abolished this activity. The crystal structure of μI-II in the presence of $Ca^{2+}$ reinforces the integrity of the active site. The key catalytic residue positions match very closely those of papain (FIG. 3). The lower $k_{cat}$ can not be inferred from the structure suggesting that subtle changes at locations beyond the immediate vicinity of catalytic residues might be the cause. The observed decrease in activity is not due to poor folding as the overall structure of the two individual domains overlap very well with the corresponding domains of the inactive human m-calpain, with expected differences around the $Ca^{2+}$ sites (FIG. 5). We believe that domains III–VI of the heterodimer augment this activity by providing supporting interactions at the bottom of the active site.

A 42 kDa autolysis fragment that stretches essentially from the same N-terminal residue (29 in μI-II, 30 in μ-, or 20 in m-) and beyond the C-terminus of μI-II (residue 356) was previously purified after autolysis of either m- or μ-calpain, and was shown to have <0.2% activity (Crawford, C., et al., *Biochem. J.* 296(Pt 1): 135–142 (1993)). The exact C-terminus for this fragment is not known, and its potential heterogeneity increases the difficulty of its elucidation by available techniques such as C-terminal sequencing or mass spectrometry. The approximate ten fold difference in activity between this fragment and our construct could be explained if its C-terminus indeed contained an inhibitory sequence. The extra fourteen amino acid extension, which contains the histidine tag native to the pET24d vector, at the C-terminus of one version of our construct does not interfere with activity, suggesting the need for a specific inhibitory sequence in this region. A more likely explanation is that the activity of the autolysis fragment drops due to the intrinsic instability of the fragment in vitro. We have observed that in spite of keeping μI-II preparations in well buffered solutions with saturating reducing agent, after few days there is a considerable decrease in activity and this correlates with an altered intrinsic tryptophan fluorescence during $Ca^{2+}$ titrations. To prevent this process we prefer to flash freeze our samples in liquid nitrogen for storage. In light of our results the physiological implications of this autolysis fragment has to be revisited. Our construct has a very similar $Ca^{2+}$ requirement for activation (~40 μM) as intact μ-calpain (5–50 μM). Moreover, in the presence of $Ca^{2+}$ this construct becomes much more resistant to proteolysis by trypsin or chymotrypsin than in the absence of the divalent cation (Moldoveanu, T., et al., *Biochim. Biophys. Acta* 1545: 245–254 (2001)), being also stable to autodigestion (FIG. 1D). The tightening of floppy loops as well as collapse of the two domains in the active structure supports this resistance to digestion. There is a possibility that this construct is generated during pathological conditions where the $Ca^{2+}$ homeostasis is altered. The generation of a weakly active yet resistant to proteolysis $Ca^{2+}$-dependent cysteine protease that has similar substrate specificity as the mother protease calpain, and probably localizes differently due to the lack of domains III–VI can result in the tissue damage phenotypes observed in pathologies implicating calpain. In such pathological states the tissue is attacked twice by calpain, initially by a shorter-lived yet hyperactive version of the molecule followed by a much longer-lived weakly active truncated calpain.

Of the pathological states that calpain has been implicated in, Alzheimer's disease has recently drawn some attention. Several groups have reported that calpain precisely cleaves the neuron specific activator p35 of the cyclin-dependent kinase 5 (cdk5) to a shorter form, p25 (Lee, M. S., et al. *Nature* 405: 360–364 (2000)). Moreover, amyloid β-peptide $A_β$ (1–42) can induce this cleavage which results in the release of the kinase from the membranes into the cytoplasm (Patrick, G. N., et al. *Nature* 402: 615–622 (1999)). There it can hyperphosphorylate tau and cause this to dissociate from microtubules and aggregate into tau tangles which correlate with neuronal degeneration. Deregulated cdk5 signaling was observed in the brains of people with Alzheimer's disease.

In spite of the absolute necessity for a calpain specific inhibitor, no active-site-directed inhibitors are calpain specific, as they also react with other cysteine proteases and/or the proteosome. Our µI-II construct in the presence of $Ca^{2+}$ is the best available target for rational inhibitor design. Aside from showing the common cysteine protease organization of active site residues, µI-II binds and is inhibited by commonly used synthetic calpain inhibitors such as E64, leupeptin, and calpain inhibitor I. The structures of inhibitor-µI-II complexes should better resolve the substrate-binding cleft of calpain, which should allow the engineering of more specific calpain inhibitors. Moreover, inhibitors can be designed to prevent any of the structural changes associated with $Ca^{2+}$-binding in domains I and II, in addition to targeting the formed active site, as seen for Wang's group PD150606 inhibitor with an elegant mechanism of calpain inhibition by binding the small subunit. µI-II construct is also a great source of calpain active site that can be used for large-scale inhibitor screens. The yields in *E. coli* are much better than those of any other known heterologously expressed recombinant calpain constructs. Moreover, the increased stability of µI-II versus that of heterodimeric calpain in the presence of $Ca^{2+}$ can allow for the design of much more versatile screening assays.

The regulation by $Ca^{2+}$ of the conventional calpains (µ- and m-) has been difficult to address at a molecular level mainly due to heterogeneity of conformations achieved at different levels of $Ca^{2+}$. These calpains exist as stable heterodimers in the absence of $Ca^{2+}$. High levels of this heterodimeric form have only been attained in heterologous expression systems based on *E. coli* (Elce, J. S., et al., *Protein Eng* 8: 843–848 (1995)) and insect cell lines (Meyer, S. L., et al., *Biochem. J.* 314 (Pt 2): 511–519 (1996)), having very similar biochemical properties as the endogenous calpain. The crystal structure of the inactive m-calpain heterodimer was solved both from rat (Hosfield, C. M., et al, *EMBO J.* 18: 6880–6889 (1999)) and human (Strobl, S., et al., *Proc. Natl. Acad. Sci. U.S. A* 97: 588–592 (2000)), revealing the circular arrangement of domains. The observed stability of the apo-m-calpain heterodimer was easily explained from the crystal structure, which shows the extensive contacts that the large subunit makes with the small subunit (Yoshizawa, T., et al., *Biochem. Biophys. Res. Commun.* 208:376–383 (1995)). In the presence of $Ca^{2+}$ major changes in conformation are postulated (limited proteolysis). One of the consequences of $Ca^{2+}$ binding is dissociation of the small subunit. The stability of the large subunit under such conditions is significantly decreased resulting in self-aggregation especially at concentrations required for high-resolution structural studies. These observations render heterodimeric samples of calpain in the presence of $Ca^{2+}$ less than optimal for structural studies such as crystallography or NMR. A reductionist approach, routine commonly employed in structural biology including protease structure determination (Kim, J. L., et al., *Cell* 87:343–355 (1996); Love, R. A., et al., *Cell* 87: 331–342 (1996)), has proved to be useful in addressing the calpain structure in the presence of $Ca^{2+}$. Our structural and biochemical data shows that the active site region of calpain can bind two $Ca^{2+}$ ions at close to physiological levels (0.5 mM $CaCl_2$). There is one unique $Ca^{2+}$site in each domain positioned quite distant from the active site cleft. Neither of these sites could be predicted from the inactive heterodimer structure. Interestingly, during modeling studies of the protease region of the human m-calpain heterodimer into the active form, Strobl and colleagues (Strobl, S., et al., *Proc. Natl. Acad. Sci. U.S.A.* 97: 588–592 (2000)) have postulated the possible $Ca^{2+}$-bridging of domains I and II, via two pairs of acidic residues found in close proximity thought to cause their repulsion. Coincidentally, two of the predicted residues, D96 and E321, are actual $Ca^{2+}$-coordinating residues in µI-II even though there is no $Ca^{2+}$ bridging between the domains. Once the active site is formed, the catalytic mechanism in calpain is expected to be identical to that of papain, as no $Ca^{2+}$ was found near the active site cleft of calpain.

Coordinating residues for both $Ca^{2+}$ ions are located on highly mobile loops that are structurally distant in the absence of $Ca^{2+}$, yet that can collapse onto the $Ca^{2+}$ ion. In spite of the dual-loop $Ca^{2+}$ coordination in µI-II, which differs from the single-loop coordination observed for the universal $Ca^{2+}$-binding motif of EF-hand-containing domain IV and VI, $Ca^{2+}$ coordination in domain II shows the canonical pentagonal bypiramid geometry observed in most studied EF-hands. The less-ordinary eight-oxygen coordination is observed in domain I. As previously discussed, a secondary role for the $Ca^{2+}$ sites is to increase the stability of the active site region as three of the four $Ca^{2+}$-coordinating loops are much more exposed in the inactive heterodimer structure, becoming protected when $Ca^{2+}$ binds. Nevertheless, the primary role of the $Ca^{2+}$ sites is to regulate active site assembly in a cooperative manner.

It is difficult to integrate the effects of domains III-VI on the active site region of calpain in the presence of $Ca^{2+}$. An initial hypothesis, that prior to active site assembly the tension directly imposed by the anchor on one side and domain III on the other side of the protease region have to be lessened, remains valid (Hosfield, C. M., et al., *EMBO J.* 18: 6880–6889 (1999); Strobl, S., et al., *Proc. Natl. Acad. Sci. U.S.A.* 97: 588–592 (2000)). On the anchor side, this tension has to be released either by heterodimer dissociation or anchor release from the small subunit. On the opposite side the release of tension is a more complex event that might be accomplished by disrupting critical salt-link interactions such as E504-K234 of m-calpain at the interface of domains II and III (Hosfield, C. M., et al., *J. Biol. Chem.* (2000)). It can also occur due to subtle structural changes between domains III and IV potentially implicating the linker. In that regard it is interesting to note that one of the insertions in the muscle specific isoform p94 occurs in the linker region (residues 514–530 of m-calpain). Once the tension is overcome the intrinsic ability of domain I and II to bind $Ca^{2+}$ should suffice for active site assembly. Domain III–VI might further enhance the $Ca^{2+}$ affinity of the active site region just as they augment its activity. We conclude that the total number of $Ca^{2+}$ atoms present in conventional calpains at 1 mM $CaCl_2$ is probably more than 5 (domains I, II, and VI), and likely 8 (domain IV). Whether the C2-like domain III has any $Ca^{2+}$ bound has to be determined structurally, this being a challenging project due to its intrinsic instability when expressed in isolation (Tompa, P., et al., *Biochem. Biophys. Res. Commun.* 280: 1333–1339 (2001)).

The structure-based activation mechanism of µI-II by $Ca^{2+}$ is evolutionarily conserved in most of the calpain large subunit isoforms: (i) $Ca^{2+}$-binding in domain I, (ii) repositions R104 side chain, which via a double salt-link interaction with the side chain of E333, (iii) triggers E333's peptide flip in domain II. (iv) This exposes the first $Ca^{2+}$-coordinating residue in the second $Ca^{2+}$ site (v) followed by $Ca^{2+}$-induced conformational changes in domain II that (vi) allow the formation of a hydrophobic pocket to accommodate W298's side chain. (vii) This side chain swings away from in between domains I and II and into this pocket (viii) therefore allowing the collapse of the two domains in the active conformation. There are 10 different calpain isoforms in the human genome, homologous in the cysteine protease region to the conventional µ-calpain. Of these, calp1-3, 5, 8, 9, and 11 have identical residues at the five critical positions that coordinate $Ca^{2+}$ via side chain interactions (FIG. 7A and B; calp11 not shown). The rat stomach-specific n-CL2 isoform is the human homologue of calp8. calp9 is also known as n-CL4 (Lee, H. J., et al. *Arch. Biochem. Biophys.* 362:22–31 (1999)), while calp5 is the human homologue of tra3. Of the other 3 isoforms calp6 has a lysine instead of the active site cysteine, therefore expected to be inactive. Calp7 has none of the observed $Ca^{2+}$-coordinating residues at the five positions, and its mouse homologue is thought to be a $Ca^{2+}$-independent protease. Calp10, isoform that has been genetically linked to diabetes mellitus (Horikawa, Y. et al., *Nat. Genet.* 26:163–175 (2000)), shows variation at 4 of the five critical $Ca^{2+}$-binding positions, thus expected to be differently regulated, if at all, by $Ca^{2+}$ at the active site. Five of the seven isoforms that have conserved $Ca^{2+}$-binding residues, calp 1–3, 8, and 9, have inherited the R and E at corresponding positions 104 and 333 of µI-II, respectively. We suggest that approximately half of the calpain homologues undergo a $Ca^{2+}$-dependent activation based on the proposed mechanism. The sigmoidal shape of the intrinsic tryptophan flurescence intensity during $Ca^{2+}$-titrations should provide a good diagnostic assay for $Ca^{2+}$-induced activation mechanism, considering that all nine tryptophan residues in the active site of µ-calpain are conserved from *C. elegans* to *D. melanogaster* to human isoforms (FIG. 7A and B). Calp5 and 11 probably bind $Ca^{2+}$ in a similar fashion, but the structural basis for cooperativity between the two sites remains to be elucidated as instead of arginine at positions 104 the residue is serine or proline, respectively. It is interesting to note that the active site region of p94 (calp3) contains the same $Ca^{2+}$-binding determinants yet it is thought to be $Ca^{2+}$ independent (Ono, Y. et al., *J. Biol. Chem.* 273: 17073–17078 (1998)). Perhaps the insertion, IS1, in domain 2 might cause it to be $Ca^{2+}$ independent by providing an already positioned hydrophobic pocket for W349 (W298 in µ-calpain); IS1 stretches right before the $Ca^{2+}$-induced antiparallel sheet µ9–µ10 (FIG. 7A and B). The atypical isoforms of calpain lack either domain IV (calp5 and tra3), both domains III and IV (n-CL2', a splice variant of n-CL2 that ends in domain III), or have a protease region linked to other domains (novel domain III of tra3). Our data support the evolution of calpain from papain by the addition of a $Ca^{2+}$ switch to the active site of the latter. Further gene fusion resulted in atypical calpains, or the typical calpains by fusion with a calmodulin-like gene. The addition of a calmodulin-like domain added another level of $Ca^{2+}$ regulation, as it did its ability to interact with the small subunit. Nevertheless, a more conserved aspect during calpain evolution has been the ability to bind $Ca^{2+}$ in the active site region.

Example 2

µI-II Binds $Ca^{2+}$ and is a $Ca^{2+}$-dependent Cysteine Protease

The active site of m-calpain in the absence of $Ca^{2+}$ is not formed as shown in the rat (Hosfield, C. M., et al, *EMBO J.* 18:6880–6889 (1999)) and human (Strobl, S., et al., *Proc. Natl. Acad. Sci. U.S.A.* 97:588–592 (2000)) structures. From examining the inactive structures it is evident that well-defined interactions on either side of the active site domains I and II could keep the active site domains apart. The independent expression of the active site domains I+II was therefore expected to be free of destabilizing interactions from neighboring regions and perhaps show activity. We undertook this experiment and to our surprise the construct containing solely the active site of µ-calpain, µI-II was inactive; that is in the absence of $Ca^{2+}$. The µI-II construct extends from the second calpain autolysis site, residue 29, which defines the start of domain I, to the end of domain II (residue 356). Its domain boundaries were chosen on the basis of the recently solved crystal structure of the m-calpain heterodimer (Hosfield, C. M., et al., *EMBO J.* 18:6880–6889 (1999)). There is over 60% identity between m- and µ-calpain in these two active-site-containing domains that make up the protease region, suggesting a great similarity between their structures.

Calpain typically produces a limited cleavage of its substrates and tends to cut between domains. To test domain I-II for in vitro proteolytic activity we used the inactive C105S mutant of m-calpain heterodimer as its substrate. This is a natural substrate for calpain during autolysis (Crawford, C., et al., *Biochem. J.* 296(Pt. 1):135–142 (1993); Nishimura, T. and Goll, D. E., *J. Biol. Chem.* 266:11842–11850 (1991)). It is easily produced in *E. coli* (Elce, J. S., et al., *Biochem. J.* 326(Pt. 1):31–38 (1997)), and is completely inactive due to the swap of the active site Cys by Ser (Elce, J. S., et al., *Protein Eng.* 8:843–848 (1995)) (FIG. 1A). At an enzyme to substrate ratio of 1:66 and in the presence of 1 mM $CaCl_2$, µI-II cuts the large subunit of C105S to generate 55 kDa, 40 kDa, and 24 kDa fragments. Compared to intact m- or µ-calpain the µI-II construct is weakly active, because digestion of the large subunit (80 kDa) was incomplete after 20 hours (FIG. 1A) compared to ~20 minutes for the intact enzymes (data not shown). Nevertheless, the activity is strictly $Ca^{2+}$-dependent as no proteolysis was observed in its absence or when $Mg^{2+}$ was substituted for $Ca^{2+}$ (FIG. 1A, lane 1). Moreover, the digestion profile was highly reminiscent of the usual m-calpain autolysis profile (55 kDa, 40 kDa, and 24 kDa major fragments), suggesting similar substrate specificity for the two proteases. In order for $Ca^{2+}$ to activate calpain there has to be a major conformational change that brings the active site Cys into register with the other catalytic residues (Hosfield, C. M., et al., *EMBO J.* 18:6880–6889 (1999)). Evidence for this change has come from partial proteolysis experiments, which show increased protection of regions between domains I and II when $Ca^{2+}$ is present (Moldoveanu, T., et al., *Biochim. Biophys. Acta* 1545: 245–254 (2001)).

The $Ca^{2+}$-dependence of domain I-II proteolytic activity led us to look for a conformational change in the protease region using intrinsic tryptophan fluorescence during real time $Ca^{2+}$ titration. A regular sigmoidal increase in intrinsic tryptophan fluorescence was observed with increasing $Ca^{2+}$ concentrations (FIG. 1B). This suggested at least two cooperative $Ca^{2+}$ binding sites contribute to the conformational change that significantly affects the environment around the tryptophans in these constructs. The total increase in the fluorescence intensity was ~36.8±0.5% (FIG. 1B, inset). The increase was first noticeable at ~5 µM $CaCl_2$, and was >99% complete at ~500 µM $CaCl_2$ (FIG. 1B). The half-maximal change in fluorescence occurred at 41.8±7.1 µM $CaCl_2$, which falls in the range of values reported for half-maximal activation of intact µ-calpain (5–50 µM). When the raw data from the titration was fitted to the Hill equation, it gave a Hill coefficient of 2.72±0.42, suggesting positively cooperative $Ca^{2+}$ binding at two or more sites is involved in this conformational change (FIG. 1B). $MgCl_2$, $MnCl_2$, and $ZnCl_2$, even at concentrations up to 30 mM, were unable to substitute for CaCl$_2$ in the observed intrinsic tryptophan fluorescence change. The change was completely reversed by EDTA (data not shown).

Figure 1C:
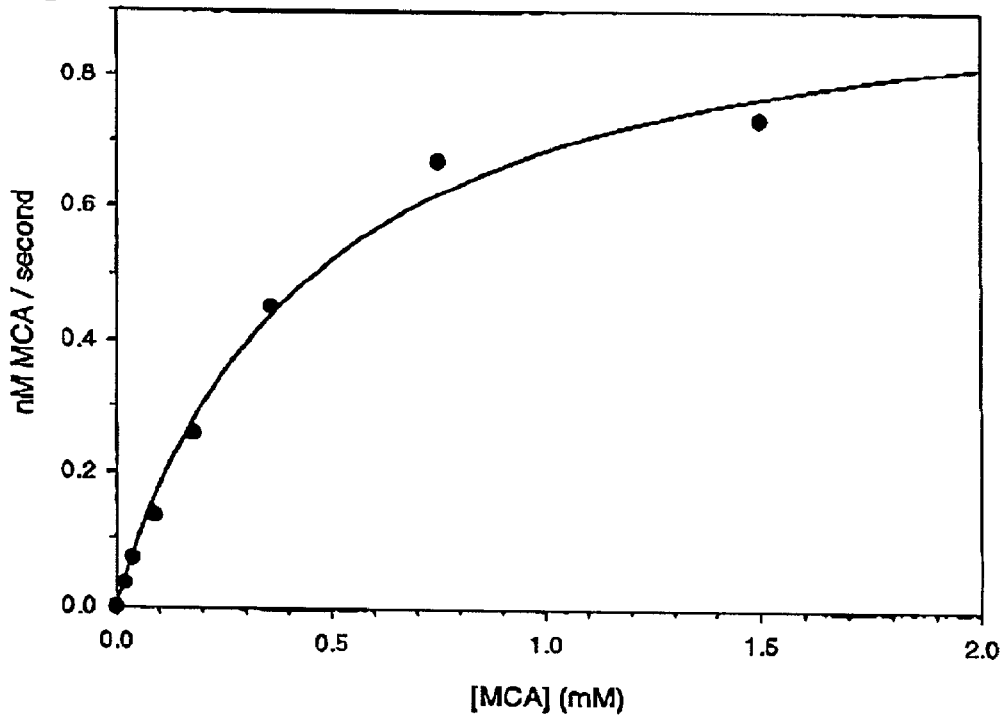

The proteolytic activity of μI-II construct against the commercially available synthetic peptide substrate SLY-MCA was tested. Just as observed for the intrinsic tryptophan fluorescence change, μI-II digested SLY-MCA only in the presence of CaCl$_2$ (FIG. 1C), and not with MgCl$_2$, MnCl$_2$, nor ZnCl$_2$ even at concentrations up to 30 mM (data not shown). The Michaelis-Menten kinetic parameters obtained for SLY-MCA digestion in the presence of 0.5 mM CaCl$_2$, K$_M$ 0.466±0.008 mM and k$_{cat}$ (4.18±0.46)×10$^4$ s$^{-1}$, indicate that μI-II is weakly active even though that CaCl$_2$ concentration results in a complete (>99%) conformational change as monitored by intrinsic tryptophan fluorescence of μI-II. Compared to intact m-calpain (K$_M$ 0.194±0.021 mM, k$_{cat}$ 0.014±0.001 s$^{-1}$) the μI-II protease region is a much less efficient enzyme, mainly due to a 35-fold decrease in turnover (k$_{cat}$); unfortunately we were unable to express the entire μheterodimer for a direct comparison, but the originally reported values for m- and μ-calpain purified from natural sources reinforces the similarity in the SLY-MCA kinetics between the two isoforms (Sasaki, T., et al., *J. Biol. Chem.* 259:12489–12494 (1984)). Moreover, as observed with the intact enzymes the activity of μI-II was inhibited by E64, leupeptin, and calpain inhibitor I (not shown), suggesting that the active site conformation in μI-II is similar to that of the protease region in the full enzymes.

We have reported previously the stabilization in the presence of Ca$^{2+}$ of a proteolytic fragment containing domains I and II which can be generated either by autoproteolysis (Crawford, C., et al., *Biochem. J.* 296(Pt 1): 135–142 (1993); Nishimura, T., and Goll, D. E., *J. Biol. Chem.* 266: 11842–11850 (1991)), by trypsin, or by chymotrypsin digestion (Moldoveanu, T., et al., *Biochim. Biophys. Acta* 1545:245–254(2001)). We reinforce this fragment's resistance to digestion in the presence of Ca$^{2+}$ by showing that μI-II is highly resistant to autoproteolysis (FIG. 1D) or to proteolysis by trypsin (not shown). In the presence of 1 mM CaCl$_2$ a gradual progression of digestion is observed throught the incubation period. Over 50% of μI-II is still present even after 20 hours of autodigestion. The overlapping N-terminal sequence and similarity in length (fragment 42 kDa, μI-II 40 kDa including the 8 residue C-terminal histidine tag) between μI-II and the protease resistant domain I-II fragment suggests a physiological relevance for this fragment as a weekly active yet digestion resistant cysteine protease that is released during autoproteolysis of the intact heterodimer.

Example 3

Overall Structure

Over most of the structure, the Ca$^{2+}$-bound structure of μI-II is very similar to that of domains I and II from the inactive rat (Hosfield, C. M., et al., *EMBO J* 18:6880–6889 (1999)) or human (Strobl, S., et al., *Proc. Natl. Acad. Sci. U.S.A.* 97:588–592 (2000)) m-calpain heterodimer. The secondary structure elements and their arrangement as observed in the inactive human structure match very closely those of the μI-II structure (FIG. 2). Domain I maintains the core α-helix (α5) surrounded by two β-sheets on one side and a cluster of α-helices on the other side. In addition to the two antiparallel β-sheets that form the core of domain II in the inactive structure, a new antiparallel β-sheet is formed between the short strands β9 and β10 (FIG. 2B) which are not interacting in the inactive structure. The two most significant structural differences between the active and inactive forms are the presence of two Ca$^{2+}$ ions, one bound at each domain, and the difference in the relative arrangement of the two domains. Looking down the α-helix (α3) harboring the active site S115 (front view; FIG. 2A) both Ca$^{2+}$ ions appear to occupy surface accessible positions in between two structurally adjacent loops. The arrangement of Ca$^{2+}$ relative to the active site residues can be observed in the top view (FIG. 2B). The binding of Ca$^{2+}$ results in major rearrangements of the loops that contain Ca$^{2+}$-coordinating residues. In the inactive structure the two domains are kept apart by ~5° rotation of the domains relative to one another and ~1–2 Å translation away from one another, as indicated by modeling studies of the active site (Hosfield, C. M., et al., *EMBO J.* 18: 6880–6889(1999)). In the presence of Ca$^{2+}$ the two domains are much closer together and rotated relative to one another such that the catalytic triad is similar to that observed in other cysteine proteases.

Example 4

A Closer Look at the Catalytic Residues of μI-II

The initial cloning of calpain suggested a fusion of a papain-like cysteine protease with a calmodulin-like protein (Ohno, S., et al., *Nature* 312:566–570 (1984)). The structure of the inactive m-calpain homodimer reinforces this notion showing how domains I and II, which form the cysteine protease region, structurally resemble the two domains that make up other cyteine proteases, such as papain and the cathepsins. The Ca$^{2+}$-bound μI-II structure extends this homology by defining the spacing between critical active site residues that are highly conserved among the various cysteine proteases. To show the striking similarity between the catalytic residues of active calpain and papain the side chains of the active site S115, H272, N296, Q109, and W298 of calpain were overlapped onto the corresponding residues in papain (S25, H159, N175, Q19, W177; FIG. 3) with an overall rmsd of 0.85. While the distance between the active site S105 O$_\gamma$ and the imidazole N$_\delta$ of H262 of the inactive m-calpain homodimer was 10.5 Å (Hosfield, C. M., et al., *EMBO J.* 18: 6880–6889 (1999)), the distance between the same residues in the holo-Ca$^{2+}$-μI-II is 3.7 Å, just as it is in papain. The third residue of the charge relay system, N296, overlapped well with the corresponding N175 of papain. Moreover, the oxyanion hole Q109 and Q19 side chain amides showed a perfect overlap in spite of the differences in the positions of their C$_\alpha$—C$_\beta$ bond. Furthermore, while W288 of the inactive m-calpain was positioned in between domains I and II as a wedge that prevents active site assembly, it is found in a similar position as observed in papain in the Ca$^{2+}$-bound μI-II. To reinforce the structural integrity of the Ca$^{2+}$-bound μI-II, W116 position was included. This residue is part of the hydrophobic core of domain I in the vicinity of the active site cysteine. Even though its side chain was not used during the overlap it aligns almost perfectly with the corresponding W26 of papain (rmsd 0.8). The similarity of the active site residues orientation and spacing between μI-II and papain reinforce the biochemical evidence supporting activity for μI-II in the presence of Ca$^{2+}$. This overlap suggests that the mechanism of catalysis of calpain is very similar if not identical to other cysteine proteases.

Example 5

Two Novel $Ca^{2+}$ Binding Sites Reside in the Cysteine Protease Region of Calpain The μI-II structure in the presence of $Ca^{2+}$ provides direct evidence for the existence of two novel $Ca^{2+}$ binding sites in the protease region of calpain. Each $Ca^{2+}$ ion binds strictly at one of the domains, rather than bridging the two domains. Two loops accommodate the eight coordinations to the $Ca^{2+}$ in domain I (FIG. 4A, red lines). Three residues on the loop preceding the helix α3, which contains the active site S115, provide four coordinating oxygen atoms. The side chain of D106 offers two coordinations, while the backbone oxygen of V99 and G101 one each. Two other coordinations are provided by the side chain of E185, which is positioned on the loop leading the N-terminus of the core helix (α5). Hydrogen bonds stabilize these side chain conformations: i) D106 to $N_\epsilon$ of W187 and ii) E185 to S180 backbone oxygen and to V99 backbone amide (FIG. 4A, black lines). In addition, the side chain of E185 is stabilized by the positive charge conferred by the microdipole of helix α5. Two ordered water molecules donate the last two $Ca^{2+}$ coordinations. One of the water molecules is stabilized by hydrogen bonds to neighboring residues: WAT1 by T103 $O_\gamma$ and D100 backbone oxygen (FIG. 4A, black lines). It is worth noticing the symmetrical arrangement of coordinations in domain I: four of the equilateral coordinations are coplanar drawing the vertices of a quadrilateral (E185, G101, WAT1), while the other four (three for now) define a plane perfectly perpendicular to the first plane.

In domain II, the $Ca^{2+}$ binding site exhibits the more commonly observed pentagonal bipyramid coordination (FIG. 4B). Just as seen in domain I, two loops are involved in $Ca^{2+}$ binding. The loop onto which the active site W298 resides contains E302 and D309. The former has two side chain coordinations to the $Ca^{2+}$, while the later only one. The loop conformation is stabilized through an internal water molecule (WAT4) that bridges one $O_\epsilon$ of E302, to the carbonyl oxygen of W303, and to the backbone nitrogen of D309. From the second loop of the $Ca^{2+}$ binding site in domain II another side chain coordination is made by D331, while two other coordinations come from backbone oxygens of E333 and M329. The seventh coordination is provided by a water molecule (WAT3), which is stabilized by interactions to E331 $O_\delta$, and the backbone nitrogen of V327. The coordination distances in the two $Ca^{2+}$ binding sites range from 2.04 Å (WAT3) to 2.90 Å (WAT2) with the average of 2.45 Å as observed in well studied $Ca^{2+}$ binding EF-hand motifs seen in calmodulin (Blanchard, H., et al., *Nat. Struct. Biol.* 4:532–538 (1997)) as well as in domain VI homodimer of calpain (ref).

The observed sigmoidicity of the intrinsic tryptophan flourescence during $Ca^{2+}$ titration and its corelation with an increase in activity suggest that the $Ca^{2+}$ binding is cooperative. Two specific salt bridge interactions between the side chain of R104 ($N_\epsilon$ and $N_\eta$), an amino acid flanked by $Ca^{2+}$-coordinating residues of domain I, and the side chain of E333 ($O_{\delta 1}$ and $O_{\delta 2}$), an amino acid that directly coordinates $Ca^{2+}$ in domain II via its backbone oxygen, provide a structural basis for the cooperativity between the two $Ca^{2+}$-binding sites (FIG. 4C, black lines). This interaction is very tight as indicated by the crystallographic B-factors falling bellow average especially at the interacting atom positions. The inter-domain interactions around the two $Ca^{2+}$ sites are not as extensive as near the active site cleft. R104_E333 salt bridge is the strongest interaction observed between the domains close to the $Ca^{2+}$ sites. It provides a structural link for proper active site assembly. In the context of the full heterodimer additional stabilizing interactions must come from domain III.

Example 6

$Ca^{2+}$-induced Conformational Changes in the Active Site of Calpain

One of the consequences of $Ca^{2+}$-binding during intact heterodimer activation must be the removal of the inhibitory W298 positioned in between domains I and II prior to active site assembly. The structure of μI-II captured this change (FIGS. 3 and 5). The observed intrinsic tryptophan fluorescence change and the associated increase in activity with increasing $Ca^{2+}$ concentrations (FIG. 1) suggested that the conformational changes induced by $Ca^{2+}$ in the active site region might result in similar structural changes in μI-II and the full heterodimer. A comparison between the inactive and active states of the active site domains I and II, using the human m-calpain heterodimer structure as a model (Strobl, S., et al., *Proc. Natl. Acad. Sci. U.S.A.* 97:588–592 (2000)), reveals these changes.

Domain I structure of the inactive human m-calpain heterodimer (Strobl, S., et al., *Proc. Natl. Acad. Sci. U.S.A.* 97:588–592 (2000)) was overlapped with domain I from the rat μI-II structure with an overall $C_\alpha$ r.m.s. deviation of 1.27 Å (FIG. 5A). There is a good overlap for most of the secondary structure elements in domain I (r.m.s. deviation ~1.0 Å). The differences originate mainly from the tightening of the large loop around the $Ca^{2+}$ site having a $C_\alpha$ r.m.s. deviation of ~5.0 Å for the residues found in the immediate vicinity of the $Ca^{2+}$ (residues 96 to 108 of μ; m numbering lags that of μ by 10 due to a 10 residue shorter N-terminus; FIG. 5A). This loop contains three of the residues that coordinate $Ca^{2+}$ and R104, which is pulled closer towards domain I. Along with these loops there is a small movement of the associated helices (α2 and α3). Since the oxyanion hole Q99 and the active site C105 ($C_\alpha$ r.m.s. deviation of 2.11 Å) reside on the loop and helix α3, respectively, domain I $Ca^{2+}$ binding influences their proper positioning in the active site. Interestingly, E185, the fourth residue that provides two coordinations to $Ca^{2+}$ moves less due to the stabilization imposed by the core helix α5 ($C_\alpha$ r.m.s. deviation of 1.55 Å). Nevertheless, its side chain is slightly rearranged to bind $Ca^{2+}$. Of the four tryptophans in domain I none undergo a significant change in conformation or environment (not shown), suggesting that most of the observed intrinsic tryptophan fluorescence change with $Ca^{2+}$ does not originate in domain I.

The $Ca^{2+}$-induced conformational changes in domain II are even more pronounced that in domain I with the overall $C_\alpha$ r.m.s. deviation of 1.35 Å for the overlapped inactive and active forms of domain II (FIG. 5B). Just as seen in domain I, most of the secondary structure elements in domain II overlap well ($C_\alpha$ r.m.s. deviation ~0.9 Å). Obvious differences can be observed in the region flanking strands β9 and β10 (residues 254 to 269, $C_\alpha$ r.m.s. deviation of ~7.0 Å), which is not directly interacting with $Ca^{2+}$. In the presence of $Ca^{2+}$ these strands form a sheet that provides supporting van der Waals contacts to the active site W298 through the side chain of the highly conserved V269. In μI-II this tryptophan presumably acted as a wedge between the two domains before $Ca^{2+}$ binding, as seen in the m-calpain heterodimer structure (W288 in FIG. 5C). The two loops that contain the $Ca^{2+}$-coordinating residues along with helix α8, which is flanked by these, undergo a marked conformational change (residues 302 to 310 and 328 to 333, $C_\alpha$ r.m.s. deviation of ~3.0 Å). The two residues of the catalytic triad that reside in domain II (H272 0.20 Å, N296 0.96 Å) show low r.m.s. deviation in the overlap. Two out of the five tryptophans in domain II undergo a significant change in conformation (FIG. 5B). W298 becomes buried in a more favourable environment provided by the $Ca^{2+}$-induced antiparallel sheet β9-β10, while W303 undergoes an ~180° rotation of its side chain around the $C_\alpha$–$C_\beta$ bond as E302 pulls it towards the $Ca^{2+}$ site. These are probably the residues that contribute mostly to the overall change in intrinsic tryptophan fluorescence observed in the presence of $Ca^{2+}$. The overall effect of $Ca^{2+}$ binding in domains I and II is easily seen when the aligned inactive domains (FIG. 5A and B, pink) are overlapped onto the μI-II structure (FIG. 5C). $Ca^{2+}$ binding to coordinating residues induces major loop rearrangement such that R104_E333 salt bridge is formed, W298 is pulled out of the active site cleft as the two domains close up, while the active site residues are positioned for catalysis. The change in tryptophan fluorescence associated with $Ca^{2+}$ binding can be attributed mostly to the tryptophans in domain II (W298 and W303). It is interesting to note that with the exception of helix α3, which harbors the active site C115, none of the secondary structure components that undergo a $Ca^{2+}$-induced change in conformation in calpain are present in papain. Structurally, the divergent evolution of calpain as $Ca^{2+}$-dependent cysteine protease from papain can be explained by the addition of a $Ca^{2+}$-dependent switch to the core of an already existing cysteine protease.

Example 7

Figures 6B, 6C:
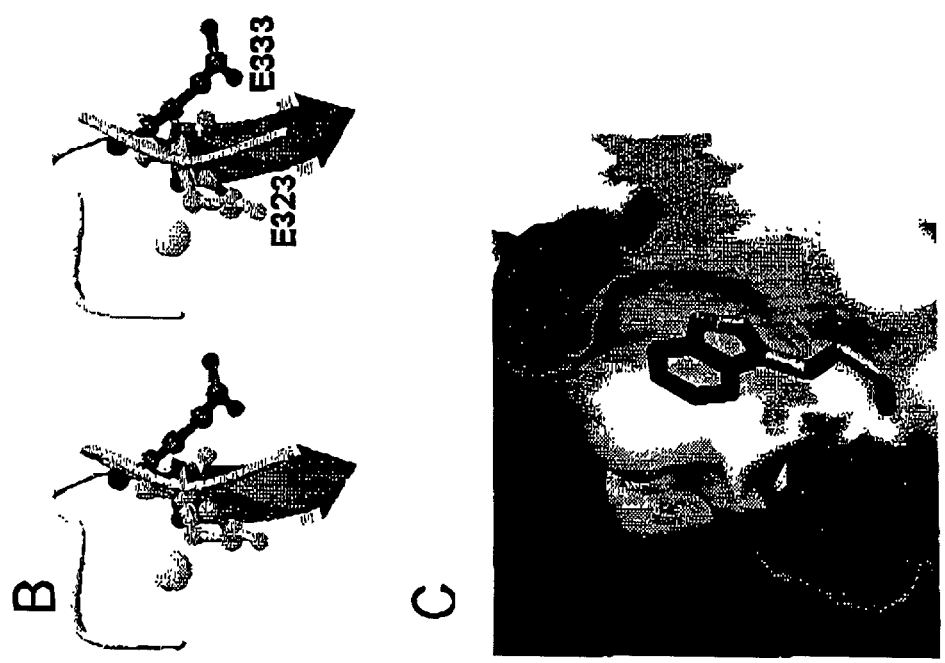

Structural Insights into the $Ca^{2+}$-dependent Activation Mechanism in the Protease Region of Calpain The detailed examination of the $Ca^{2+}$ binding sites and the $Ca^{2+}$-induced conformational changes allows us to postulate a structural mechanism of μI-II activation. We propose that $Ca^{2+}$ binds first at domain I. The already placed $Ca^{2+}$-coordinating residue E185, which moves very little upon $Ca^{2+}$ binding, can act as the nucleation site (FIG. 5A). The other three coordinating residues in domain I belong to the same loop, which rapidly assumes the $Ca^{2+}$-bound conformation. The movement of this loop is the most significant energetic barrier that $Ca^{2+}$ binding has to overcome in domain I. As this loop undergoes the $Ca^{2+}$ bound conformation, R104, which in the inactive heterodimer is surface exposed, is brought around the 328–332 loop of domain II and positioned at a less accessible site where it is ready to interact with the side chain of E333 (FIG. 6A). In domain II none of the $Ca^{2+}$-coordinating residues provide an already existing nucleation site for $Ca^{2+}$ binding (FIG. 5B). Moreover, the energetic barrier is presumably much greater than in domain I, as two loops, rather than one, have to be rearranged dramatically with the $Ca^{2+}$-coordinating residues having to travel a much greater distance than in domain I (FIG. 5B). Furthermore, the side chain of E333 in the absence of $Ca^{2+}$ (orange, FIG. 6B) causes a steric barrier to $Ca^{2+}$ binding as it overlaps the $Ca^{2+}$ position. The observed peptide bond flip at residue E333 in the presence of $Ca^{2+}$ suggests that this might be the initial event that exposes the first $Ca^{2+}$-coordinating residue in domain I. We suggest that the electropositive environment contributed by the repositioned R104 side chain is the trigger for E333 peptide bond flip, as it attracts the electronegative side chain of E333. Once exposed, the carbonyl oxygen of E333 can act as a nucleation site for $Ca^{2+}$ binding. The rest of the $Ca^{2+}$-coordinating residues can follow and assume their $Ca^{2+}$-bound conformation. The next critical event is the removal of W298 from in between the two domains. This is influenced by the side chain rearrangement of the neighboring residue E302 as it moves towards the $Ca^{2+}$ making room for the $Ca^{2+}$-induced antiparallel sheet β9-β10 to form at an adjacent site and to provide stabilizing van der Waals interactions to W298. Two conserved valine residue, V269 and V301, form a more favorable hydrophobic environment that attracts W298, which is found in a surface exposed position in between the two domains in the inactive heterodimer (FIG. 6C). Once W298 is repositioned, the two domains can come together and assume the catalytically competent conformation, with the papain-like arrangement of the key active site residues (FIG. 3). To address the mechanism of activation for the full calpain heterodimer domain III interactions with the protease region have to be considered, adding another level of complexity to our proposed mechanism for assembly of the active site.

Example 8

The Structural Determinants of a $Ca^{2+}$-dependent Cysteine Protease are Highly Conserved Among Calpain Large Subunit Homologues Even from Distantly Related Species The calpain super family encompasses isoforms that are homologous to the large subunit and to the small subunit. The former kind has been found both in vertebrates and invertebrates (reviewed in Suzuki's review). While some of these isoforms extend their homology throughout the length of the large subunit (calp1, calp2, calp3, nCL2, nCL4, calpA FIG. 7A and B), the rest only display it in the protease region (domain I and II), containing novel domains elsewhere (tra3 ref) or completely lacking other domains (nCL2', a splice variant of nCL2 that lacks domains III and IV ref). We have aligned the amino acid sequences of the rat μI-II and of few representative isoforms in order to establish whether the structural determinants for $Ca^{2+}$-dependence in the protease region are also conserved among these isoforms. The aligned isoforms have identical residues at all five side chain-dependent $Ca^{2+}$-coordinating positions (FIG. 7A and B; red highlights). Highly conserved backbone carbonyl coordinations are observed in domain I with G101 being identical in all isoforms (FIG. 7A and B; bottom, red b). This glycine potentially confers more flexibility to the $Ca^{2+}$-binding loop (FIG. 7A and B; top, pink bar). In domain II one of the carbonyl coordinations, M328, is highly variant, but the side chain should not diminish the $Ca^{2+}$-coordinating ability of the backbone carbonyl, as it is surface exposed. The highly conserved E333 position in domain II provides one carbonyl coordination, and, as seen in μI-II, might interact in the other isoforms with the highly conserved R104 (FIG. 7A and B, blue highlights). Only in C. elegans tra3, an isoform with a novel domain III at the C-terminus of the protease region, the R104_E333 interaction is not predicted, suggesting a different mechanism of $Ca^{2+}$ activation but identical $Ca^{2+}$-binding sites. In spite of disputing data on the $Ca^{2+}$-dependence of p94 (Branca, D., et al., Eur. J. Biochem. 265: 839–846 (1999)), a muscle specific isoform implicated in LGMD (Ono, Y. et al., J. Biol. Chem. 273: 17073–17078 (1998)), we postulate a similar mechanism of activation by $Ca^{2+}$ in the protease region of this isoform. In light of our structural data this alignment suggests that the $Ca^{2+}$-binding determinants evolved first followed by at least two different $Ca^{2+}$ activation mechanisms. The distant isoform from *C. elegans*, tra3, might use a different mechanism than the closer isoform from *D. melanogaster*, calpA, which probably uses a similar mechanism to the conventional calpains.

Example 9

Cloning of the Protease Region From Rat µ-calpain

The domain I-II construct from µ-calpain (µI-II) started with an N-terminal Met and extended from residue 29 ($MG^{29}RHENA$-) to residue 356, followed by a C-terminal 13 residue tail provided by the pET24d vector (Novagen) that includes a polyhistidine tag ($\rightarrow NLTPD^{356}KLAAALEH_6$). The PCR 5'-primer gcatggccatgggccgccatgaaaatgccat and 3'-primer gagcttaagcttgtcaggtgtaaggttgcagattt (Cortec nucleic acid services at Queen's University) were designed to contain the Nco I and Hind III sites (underlined), respectively, for cloning in the corresponding restriction sites available in the pET24d vector. PCR amplification was performed using Pfu DNA polymerase (Clontech) with rat calpain large subunit DNA as template (Elce, J. S., et al., *Protein Eng* 8: 843–848(1995)). The amplified product and pET24d vector were digested with Nco I and Hind III, gel purified (Qiagen gel extraction kit), ligated, and transformed into *E. coli* strain JM83. Colonies were grown under kanamycin selection and cloned inserts were sequenced (Cortec) to confirm their indentity and integrity. To perform intrinsic fluorescence measurements and crystallization in the presence of $Ca^{2+}$ without the risk of proteolysis, the active site Cys was mutated to Ser by the single-stranded method of Kunkel (Kunkel, T. A., et al., *Methods Enzymol.* 204:125–139 (1991)).

Example 10

Protein Expression and Purification

Domain I-II construct from µ-clapain was expressed in *E. coli* BL21 (DE3) under kanamycin selection. *E. coli* was grown in 4L LB broth (Fisher) at 37° C. and protein expression was induced with 0.4 M isopropyl-1-thio-β-D-galactopyranoside after the temperature was decreased to 20° C. As previously described for m-calpain (Elce, J. S., et al., *Protein Eng* 8: 843–848 (1995)), the protein was purified over four columns: DEAE-Sephacel, Ni-agarose, Sephadex G-75, and Q-Sepharose (FPLC). The domain I-II construct was detected in DEAE column eluate by immunoblotting using an anti-His-tag antibody (Clontech), and in other column profiles by SDS-PAGE. After the final purification step, domain I–II was concentrated to ~50 mg/mL in storage buffer (10 mM HEPES, pH 7.6, 10 mM DTT) in a Biomax 10K concentrator (Millipore). Aliquots (50 µL) were flash-frozen in liquid nitrogen and stored at −70° C. A 4L preparation yielded 10–40 mg of protein. The inactive, C105S, m-calpain heterodimer was purified as previously described (Elce, J. S., et al., *Protein Eng* 8: 843–848 (1995)).

Example 11

Crystallization and Structure Determination

Crystallization of the C115S µI-II construct in the presence of $Ca^{2+}$ was performed by the hanging drop method with the well solution containing 1.5 M NaCl, 2% PEG 6000, 0.1 M MES pH 6.0, 15% glycerol, and 10 mM $CaCl_2$. The drop size was less then 5 µL and contained an equal volume of well solution and of protein. The protein concentration before drop addition was 12.5 mg/mL, a four times dilution of the stock with storring buffer. Crystals grew in a few days, and prior to data collection they were cryo protected by serial soakings (for up to 5 minutes) in stabilization solutions containing 20, 25, and 30% (v/v) glycerol at a time. Diffraction data were collected on a house source using 0.5° oscillations, and processed using the HKL program suite (Otwinowski ,Z., and Minor, W., *Methods Enzymol.* 276:307–326 (1997)). The space group was C2 with two molecules per asymmetric unit. The structure was determined by the molecular replacement package AmoRe (Navaza, J., *Acta Cryst.* A50:157–163) using the structure of the $Ca^{2+}$-bound m-calpain domain I–II (mI-II) as a model. Most of the mI-II model fit the µI-II electron density map well, with the dissimilar regions being manually traced using XFIT (McRee, D. E. *J. Mol. Graph.* 10: 44–46 (1992)) aided by a few rounds of refinement in the CNS package (Brünger, A. T., *Acta Cryst.* D45: 905–921 (1998)). PROCHECK was used to asses the quality of the model with >90% of the residues lying in the most favourable regions of the Ramachandran plot and no residues in the disallowed regions.

Example 12

Activity of Domain I-II Construct Against Protein and Synthetic Peptide Substrates Proteolytic digestion of the C105S m-calpain heterodimer was performed at 22° C. in a final volume of less than 150 µL, in 50 mM HEPES pH 7.6, 1 mg/mL calpain, 0.15 mg/mL µI-II, without divalent cations, or with 1 mM $CaCl_2$ or 1 mM $MgCl_2$. Autolysis of µI-II was performed under the same conditions but instead of the C105S m-calpain substrate, 2.5 mg/mL of µI-II was used. The reaction was stopped by the addition of 2×SDS sample buffer. At specific time intervals aliquots were removed and analyzed by SDS-PAGE using a 9% gel. Control reactions lacked the protease domain I–II. The activity of µI-II against the peptide substrate SLY-MCA (Sigma) was also tested in 50 mM HEPES pH 7.6, 200 mM NaCl, 1 mM DTT, 5–30 mM divalent cation ($CaCl_2$, $MgCl_2$, $MnCl_2$, or $ZnCl_2$), 0.75 mM SLY-MCA, 2.5 µM µI-II, in a final volume of 3 mL. MCA release was monitored in a LS50B Perkin Elmer luminescence spectrometer set with excitation and the emission wavelengths at 360 nm and 460 nm, respectively. Steady-state kinetics analysis was performed under the same buffer conditions but in the presence of 0.5 mM $CaCl_2$, by varying SLY-MCA concentration from 0.02–1.5 mM. The steady-state parameters ($k_{cat}$ and $K_M$) were obtained from the Michaelis-Menten plot.

Example 13

Intrinsic Tryptophan Fluorescence Measurements of Domain I–II

Intrinsic tryptophan fluorescence measurements were performed in a Perkin Elmer LS50B fluorescence spectrophotometer at 22° C. using a stirrer-adapted 4 mL cuvette (Helmma). Excitation and emission wavelength were set at 280 nm and 340 nm, respectively. The reaction buffer was the same as that used for activity measurements against SLY-MCA, and the protein concentration was 0.65 µM. To prevent any unwanted autolysis, the inactive Cys to Ser mutant domain I–II constructs were used. $CaCl_2$ (50 mM) dissolved in the reaction buffer was pumped continuously (4 µL/min, Harvard Apparatus pump 22) using a 250 µL microsyringe (Hamilton-microliter 1000 series gastight) through a tube into the cuvette. The reaction mixture was vigorously mixed using the internal magnetic stirrer of the fluorimeter. The fluorescence intensity was corrected for dilution, and the normalised data was fitted to the Hill equation $y=x^n/k^n+x^n$), where y is the fraction of maximum intensity change, $k=[Ca^{2+}]_{0.5}$ (the value of $[Ca^{2+}]$ at which half-maximum intensity change is observed, n is the Hill coefficient, and x is $[Ca^{2+}]$. Intrinsic tryptophan fluorescence measurements were also performed under the same buffer conditions but substituting for $CaCl_2$, either $MgCl_2$, $MnCl_2$, or $ZnCl_2$ up to 30 mM. To test the aggregation state of the domain I–II constructs, relative 90° light scattering was monitored under the same reaction conditions by setting both the excitation and emission wavelength of the spectrophotometer to 320 nm. No significant aggregation was detected even at the highest $CaCl_2$ concentration (30 mM) tested.

Example 14

$Ca^{2+}$-bound µI-II in Complex with Inhibitor E64

We have demonstrated that our recombinant protease core µI-II (mini-calpain) binds specific calpain inhibitors and can, therefore, be used as a template for their design and screening. In a preliminary study the core was complexed with a common commercially available cysteine protease inhibitor, E64 (trans-epoxysuccinyl-L-leucilamido(4-guanidino)-butane). E64 and its derivative E64c were previously shown to interact at the active site of cysteine proteases such as papain (Katerelos, N. A., et al., *FEBS Lett.* 392: 35 (1996); Kim, M. J., et al., *Biochem. J.* 287: 797 (1992)), cathepsin K (Zhao, B., et al., *Nat. Struct. Biol.* 4: 109 (1997)), and actinidin (Varughese, K. I., et al., *Biochemistry* 31: 5172 (1992)) through an irreversible covalent modification of the active site nucleophilic thiol group. Since the covalent link is essential for inhibitor binding, we reacted C115 µI-II with E64 in the presence of 5 mM $CaCl_2$, 200 mM NaCl and 50 mM HEPES (pH 7.6). The µI-II-E64 protein was then separated from unreacted inhibitor by ion exchange chromatography on an FPLC Q-Sepharose column, concentrated and stored as described for the native µI-II (Moldoveanu, T., et al., *Cell* 108: 649 (2002)). This protein preparation was unable to hydrolyse SLY-MCA but bound $Ca^{2+}$ as indicated by the expected intrinsic fluorescence change. When the inhibitor was bound at the active site of papain, it was previously shown to quench the fluorescence of the active site W177. We also observed quenching of W298 fluorescence consistent with inhibitor binding at the active site. The crystallization procedure was similar to that used with native µI-II (Moldoveanu, T., et al., *Cell* 108: 649 (2002)). We obtained new conditions for µI-II-E64 that were similar to the native conditions, but lacked the PEG 6000 and the glycerol. The latter was nevertheless still used as a cryoprotectant as described for the native protein. The new crystals were of a different space group, P212121, with one molecule per asymmetric unit diffracting well at 1.8 Å resolution. The structure was solved by molecular replacement as for the native µI-II but using µI-II as a model. The refinement ($R_{cryst}$=26%, $R_{free}$=29%) follows the same steps as established for the native µI-II (Moldoveanu, T., et al., *Cell* 108: 649 (2002)).

The structures of µI-II-E64 and µI-II overlap with an r.m.s.d. of 0.291 Å for the backbone atoms, displaying an identical $Ca^{2+}$ binding mechanism and active site realignment. The observed difference occurs at the active site, where there is good density for E64 in the former structure (FIG. 8A). E64 stretches extensively across the P sites (P1-3) and modestly across the P' sites (FIG. 8A, B), as seen in other solved structures of cysteine proteases in complex with E64. The P' site interactions are, however, very tight, being buried in the molecular surface representation (FIG. 8B, C). The leucine moiety of E64 fits conveniently in the P2 pocket lined by S251 and A273 side chains, just as seen in cathepsin K (Zhao, B., et al., *Nat. Struct. Biol.* 4: 109 (1997)). In spite of the P3 position being very open (in contrast to that seen in cathepsin K complex (Zhao, B., et al., *Nat. Struct. Biol.* 4: 109 (1997)), we detected the guanidinobutane moiety of the inhibitor extending across the G207-G208 coil in the same orientation as seen in the latter structure. The P3 difference might define the selectivity of certain substrates for cathepsins (Zhao, B., et al., *Nat. Struct. Biol.* 4: 109 (1997)) over calpain.

Having now fully described the present invention in some detail by way of illustration and example for purposes of clarity of understanding, it will be obvious to one of ordinary skill in the art that same can be performed by modifying or changing the invention with a wide and equivalent range of conditions, formulations and other parameters thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of designing a ligand that binds to one or more domains of a calpain or isoform thereof, said method comprising:
    (a) crystallizing domain and domain II of said calpain or isoform thereof in the presence of a cation, said domains having protease activity;
    (b) analyzing structural features of said crystallized domain I and domain II to obtain structural information on said domain I and domain II in the presence of the cation;
    (c) utilizing said structural information to design a ligand having the ability to bind to said domain I and domain II in the presence of the cation; and
    (d) reporting the designed ligand;
    wherein crystallizing domain I and domain II does not include crystallizing other domains of said calpain or isoform thereof.

2. The method of claim 1, wherein said calpain or isoform thereof is m-calpain or µ-calpain, or a mutant, variant or derivative thereof.

3. The method of claim 1, wherein said domain I and domain II comprise one or more active sites of said calpain or isoform thereof.

4. The method of claim 1, wherein said ligand modulates the function of said calpain or isoform thereof upon binding to said domain I and domain II.

5. The method of claim 4, wherein the binding of said ligand to said domain I and domain II inhibits or reduces the function of said calpain or isoform thereof.

6. The method of claim 4, wherein the binding of said ligand to said domain I and domain II activates or enhances the function of said calpain or isoform thereof.

7. The method of claim 4, wherein the binding of said ligand to said domain I and domain II induces a conformational change in said calpain or isoform thereof.

8. The method of claim 1, wherein said ligand is a substrate for said calpain or isoform thereof.

9. A method of determining ligand binding to one or more domains of calpain or isoform thereof, comprising:
   (a) providing isolated crystallized domain I and domain II of said calpain or isoform thereof, said domains having protease activity;
   (b) providing a ligand;
   (c) mixing said ligand with said isolated crystallized domain I and domain II in the presence of a cation to form a mixture;
   (d) illuminating said mixture with light at a wavelength of about 260 to 300 nm; and
   (e) measuring the amount of fluorescence emitted by said mixture at a wavelength of about 320 to 360 nm;
   wherein a reduction in emission by said ligand-domain mixture relative to a control crystallized domain I and domain II illuminated in the absence of said ligand indicates binding of said ligand to said domain I domain II.

10. The method of claim 9, wherein said mixture is illuminated with light at a wavelength of about 280 nm.

11. The method of claim 9, wherein the fluorescence emission is measured at a wavelength of about 340 nm.

12. The method of claim 1, wherein analyzing comprises obtaining an X-ray diffraction pattern of said crystallized domains.

13. The method of claim 12, wherein said X-ray diffraction pattern has a resolution in the range of about 0.5–10.0 Å.

14. The method of claim 12, wherein said X-ray diffraction pattern has a resolution in the range of about 1.5–3.5 Å.

15. The method of claim 9, wherein the cation is calcium.

16. The method of claim 9, wherein the ligand is designed by a method comprising:
   (a) crystallizing domain I and domain II of calpain or isoform thereof in the presence of a cation, said domains having protease activity;
   (b) analyzing structural features of said crystallized domain I and domain II to obtain structural information on said domain I and domain II in the presence of the cation; and
   (c) utilizing said structural information to design a ligand having the ability to bind to said domain I and domain II in the presence of the cation;
   wherein crystallizing domain I and domain II does not include crystallizing other domains of said calpain or isoform thereof.

17. The method of claim 1, wherein the cation is calcium.

18. The method of claim 1, further comprising:
   (d) co-crystallizing the ligand with domain I and domain II of said calpain or isoform thereof in the presence of the cation to obtain a ligand-domain complex;
   (e) obtaining structural information about the ligand-domain complex; and
   (f) using said structural information to refine the design of the ligand.

19. A method of determining ligand binding to one or more domains of calpain or isoform thereof, comprising:
   (a) co-crystallizing a ligand with domain I and domain II of said calpain or isoform thereof in the presence of a cation, said domains having protease activity;
   (b) illuminating said co-crystallized ligand and domain I and domain II with light at a wavelength of about 260 to 300 nm; and
   (c) measuring the amount of fluorescence emitted by said co-crystallized ligand and domain I domain II at a wavelength of about 320 to 360 nm;
   wherein a reduction in emission by said co-crystallized ligand and domain I and domain II relative to a control crystallized domain I and domain II illuminated in the absence of said ligand indicates binding of said ligand to said domain I and domain II.

20. The method of claim 19, wherein said light has a wavelength of about 280 nm.

21. The method of claim 19, wherein the fluorescence emission is measured at a wavelength of about 340 nm.

22. The method of claim 19, wherein the ligand is designed by a method comprising:
   (a) crystallizing domain I and domain II of calpain or isoform thereof in the presence of a cation, said domains having protease activity;
   (b) analyzing structural features of said crystallized domain I and domain II to obtain structural information on said domain I and domain II in the presence of the cation;
   (c) utilizing said structural information to design a ligand having the ability to bind to said domain I and domain II in the presence of the cation; and
   (d) reporting the designed ligand;
   wherein crystallizing domain I and domain II does not include crystallizing other domains of said calpain or isoform thereof.

23. The method of claim 19, wherein the cation is calcium.

* * * * *

UNITED STATES PATENT AND TRADEMARK OFFICE
CERTIFICATE OF CORRECTION

PATENT NO. : 7,236,891 B2  Page 1 of 1
APPLICATION NO. : 10/157016
DATED : June 26, 2007
INVENTOR(S) : Peter L. Davies et al.

It is certified that error appears in the above-identified patent and that said Letters Patent is hereby corrected as shown below:

Column 34, Claim 1, Line 42
"domain and" should be --domain I and--

Column 36, Claim 19, Line 21
"domain I" should be --domain I and--

Signed and Sealed this

Sixteenth Day of March, 2010

David J. Kappos
*Director of the United States Patent and Trademark Office*